US006972182B1

(12) United States Patent
Colyer et al.

(10) Patent No.: US 6,972,182 B1
(45) Date of Patent: *Dec. 6, 2005

(54) METHODS AND COMPOSITIONS USING COILED BINDING PARTNERS

(75) Inventors: John Colyer, West Yorkshire (GB); Joanne Lightowler, York (GB)

(73) Assignee: Cyclacel, Ltd., Dundee Technopole (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/259,474

(22) Filed: Feb. 26, 1999

(51) Int. Cl.⁷ .................. G01N 33/573; G01N 33/53

(52) U.S. Cl. ................. 435/7.4; 435/4; 435/7.1; 435/7.8; 435/7.9; 530/300; 530/350

(58) Field of Search ................. 435/4, 5, 6, 7, 435/7.1, 7.23, 7.21, 7.8, 17, 501, 691, 697, 193, 252.31, 254.2, 320.1; 530/350, 395; 536/23.5, 23.4; 514/418, 486

(56) References Cited

U.S. PATENT DOCUMENTS

| 5,605,809 A | * | 2/1997 | Komoriya et al. | 435/23 |
|---|---|---|---|---|
| 5,714,342 A | * | 2/1998 | Komoriya et al. | 435/23 |
| 5,726,027 A | * | 3/1998 | Olefsky | 435/7.21 |
| 5,834,504 A | * | 11/1998 | Tang et al. | 514/418 |
| 5,856,162 A | * | 1/1999 | Schlessinger et al. | 435/196 |
| 6,465,199 B1 | * | 10/2002 | Craig et al. | 435/7.4 |

FOREIGN PATENT DOCUMENTS

| WO | WO-92/00388 | * | 1/1992 | C12Q/1/68 |
|---|---|---|---|---|
| WO | WO96/13607 | | 5/1996 | |
| WO | WO97/28261 | | 8/1997 | |
| WO | WO-97/28261 | * | 8/1997 | C12N/15/12 |
| WO | WO 97/37037 | * | 10/1997 | C12Q/1/42 |
| WO | WO 98/06737 | * | 2/1998 | C07H/21/04 |
| WO | WO 98/07835 | * | 2/1998 | C12N/9/00 |

OTHER PUBLICATIONS

Kinjo et al., "Ultrasensitive hybridization analytsi using fluorescence correlation spectroscopy.", Nucleic Acids Research, 1995, vol. 23, No. 10, pp. 1795–1799.*
Adler, et al., *Methods in Enzymology*, 27:675–796 (1973).
Atherton, et al., *J. Chem. Soc.*, 1981:538–546 (1981).
Bowles and Pappin, *Trends in Biochemical Science*, 13:60–64 (1988).
Brown and Vaughan, *Circulation*, 97:1411–1420 (1998).
Carrington, et al., *Journal of Virology*, 62:2313–2320 (1988).
Casey and Seabra, *Journal of Biological Chemistry*, 271:5289–5292 (1996).
Crick, *Acta. Crystallogr.*, 6:689–697 (1953).
Crowley, et al., *Cell*, 73:1101–1115 (1993).
Cryns, et al., *J. Biol. Chem.*, 271:31277–31282 (1996).
Eigen and Rigler, *PNAS (USA)*, 91:5740–5747 (1994).
Elson and Magde, *Biopolymers*, 13:1–27 (1974).
Fields and Song, *Nature*, 340:245–246 (1989).
Fushman, et al., *J. Biological Chemistry*, 273:2835–2843 (1998).
Gonzalez, et al., *Nature Structural Biology*, 3:1011–1018 (1996).
Hahn, et al., *PNAS (USA)*, 89:2679–2683 (1992).
Hayashi, et al., *Journal of Biological Chemistry*, 248:2296–2302 (1973).
Hedo, et al., *Journal of Biological Chemistry*, 258:10020–10026 (1983).
Hicks, et al., *Folding and Design*, 2:149–158 (1997).
Horiuchi, et al., *Mol. Cell. Biol.*, 12:4515– (1992).
Itoh, et al., *J. Biol. Chem.*, 268:3025– (1993).
Johnson, et al, *Biochemistry*, 15:569–575 (1976).
Jovin and Jovin, *Cell Structure and Function by Microspectrofluorometry*, E. Kohen and J.G. Hirschbrg, Academic Press (1989).
Kinjo and Rigler, *NAR*, 23:1795–1799 (1995).
Kinoshita, et al., *J. Biochem.*, (Tokyo) 122:251–257 (1997).
Klauck, et al., *Science*, 271:1589–1592 (1996).
Kodukula, et al., *Journal of Biological Chemistry*, 266:4464–4470 (1991).
Konishi, et al., *Biochem. And Biophys. Res. Communications*, 205:1770–1775 (1994).
Lakowicz, *Principles of Fluoroscence Spectroscopy*, Plenum Press, New York (1983).
Lumb, et al., *Biochemistry*, 33:7361–7367 (1994).
Lumb and Kim, *Biochemistry*, 34:8642–8648 (1995).
Matthias, et al., *NAR*, 17:6418 (1989).
Máytus, *J. Photochem. Photobiol. B: Biol.*, 12:323–337 (1992).
Mergener and Baillie, *J. British Medical Journal*, 316:44–48 (1998).
Miller, *Ann. Rev. Microbiol.*, 42:177–199 (1988).
Nautiyal, et al., *Biochemistry*, 34:11645–11651 (1995).
O'Shea, et al., *Science*, 243:538–542 (1989).
Parks, et al., *Analytical Biochemistry*, 216:413–417 (1994).
Merrifield, *J. Am. Chem. Soc.*, 85:2149–2154 (1963).
Puls, et al., *Proc. Natl. Acad. Sci. USA*, 94:6191–6196 (1997).
Rigler, et al., in *Fluorescence Spectroscopy New Methods and Applications*, Springer Verlag, p. 13–24 (1992).

(Continued)

Primary Examiner—Long V. Le
Assistant Examiner—Lisa V. Cook
(74) Attorney, Agent, or Firm—Kathleen M. Williams; Palmer & Dodge, LLP

(57) ABSTRACT

The present invention relates to a polypeptide multimer comprising a first polypeptide having associated therewith a label and a second polypeptide, wherein a) at least one of the polypeptides is susceptible to protease digestion; b) association of the polypeptides to form a multimer is detectable via a signal emitted by the label; and c) digestion of at least one polypeptide results in dissociation of the multimer and modulation of the signal emitted by the label, and the method of detecting or monitoring the activity of a protease enzyme based on such a multimer.

12 Claims, 4 Drawing Sheets

OTHER PUBLICATIONS

Ron and Mochly–Rosen, *Proc. Natl. Acad. Sci. USA,* 92:492–496 (1995).

Sambrook, et al., *Molecular Cloning: A Laboratory Manual,* 2nd ed., Cold Spring Harbor Laboratory Press, Clod Spring Harbor, NY (1989).

Schumacher, et al., *Science,* 271:1854–1857 (1996).

Spatola, in *Chemistry and Biochemistry of Amino Acids, Peptides and Proteins,* Weinstein, ed., Marcel Dekker, NY, p. 267 (1983).

Studier, et al., *Methods in Enzymol.,* 185:60–89 (1990).

Su, et al., *Biochemistry,* 33:15501–15510 (1994).

Thornberry, et al., *Journal of Biological Chemistry,* 272:17907–17911.

Thornberry and Lazebnik, *Science,* 281:1312–1316 (1998).

Wang, et al., *J. Biol. Chem.,* 272:17542–17550 (1997).

Yan, et al., *J. Mol. Biol.,* 275:25–33 (1998).

\* cited by examiner

FRET         NO FRET

UNFOLDED POLYPEPTIDE MOLECULE - NO FRET.

FOLDED FRET     UNFOLDED + CLEAVED
NO FRET

WIQALEQEIQALEQENAALEKEIKKLEKEIAALAAIAALAAAI (SEQ ID NO: 31) (i)

KIQALRQRIQALRQRNQALRQRIQALRQRIQALQQQIQALQQQI (SEQ ID NO: 32) (ii)

- FOLATE RECEPTOR SEQUENCE     - LEADER SEQUENCE

☐ D-AMINO ACID COILED COIL SEQUENCE
— L-AMINO ACID SEQUENCE (CONTAINING MODIFICATION SITE)

METHODS AND COMPOSITIONS USING COILED BINDING PARTNERS

FIELD OF THE INVENTION

The present invention relates to a method for detecting or monitoring the activity of an enzyme. In particular, the invention relates the use of a polypeptide multimer capable of generating a multimerisation-dependent signal and whose multimerisation properties are modulated by the activity of a protease in such a method.

BACKGROUND

Proteolysis has long been recognised as an important intra- and extracellular modification of proteins. Endopeptidase enzymes recognise particular primary sequence signals (and sometimes also secondary or tertiary structural cues) within a substrate protein and cleave the peptide bond following a particular amino acid. Exopeptidases, on the other hand, digest polypeptides from the N or C terminus. Exopeptidases are generally not sequence-specific. These enzymes play a role in, for example, digestion, the coagulation of blood, the complement cascade and the destruction of inactive, mutated or foreign forms of proteins in the cell. Proteolysis is also important as a method of, recycling amino acids within the cell for the synthesis of new proteins or for utilisation as a fuel source. More recently, the role of proteolysis in signalling and in specific intracellular processes has been recognised.

It is clear that aberrant proteolysis plays a significant role in a number of disease processes. Examples include the processing of β-amyloid precursor protein (inappropriate processing of this protein is thought to play a role in Alzheimer's Disease), the inappropriate activation of proteolytic enzymes of digestion leading to pancreatitis and a loss of proteolysis of the insulin receptor precursor leading to diabetes. Proteolysis is now understood to play important roles both within the cell and in processes important in homeostasis in multi-cellular organisms. These include:

Production of bioactive molecules from inactive precursors. A hallmark of proteolytic enzymes is their production in many cases as inactive proenzymes and their subsequent rapid activation by a proteolytic event. This may be an autocatalytic process or part of a cascade. This is exemplified by the blood clotting cascade and also the cleavage of digestive proproteases to their active form. One of the central events in acute pancreatitis is the premature proteolysis and activation of pancreatic enzymes (especially trypsin) leading to autodigestion of pancreatic tissue amongst other effects (Acute pancreatitis, Mergener, K & Baillie, J. British Medical Journal (1998) 316 44–48). Proteases are also known to activate other proenzymes and to play a role in the generation of other bioactive molecules. An important clinical example of this is the generation of angiotensin II by the enzyme angiotensin converting enzyme (ACE). ACE cleaves the C-terminal two residues from the inactive angiotensin I to produce the active form, angiotensin II. Angiotensin II has potent vasoconstrictive and salt-retentive properties, the control of ACE activity by ACE inhibitors has an important clinical role in the treatment of hypertension, heart failure, myocardial infarction and diabetic nephropathy (Angiotensin converting enzyme inhibitors, Brown NJ. & Vaughan, DE., Circulation (1998) 97 1411–1420).

Destruction of bioactive molecules. An important aspect of a regulatory process is the presence not only of an 'on switch' but also the potential to switch it off again. This is an area in which proteolysis is particularly important as it is an irreversible modification. The only way in which the process can be restarted is by a resynthesis of the destroyed component. This affords a high level of control over timing. An important clinical example of this is the degradation of bradykinin by ACE. Bradykinin has a number of effects in the body including inducing smooth muscle contraction, increasing vascular permeability and promoting vasodilation and natriuresis. This, together with the example above, indicates that ACE is important in the regulation of the balance between the antagonistic effects of angiotensin II and bradykinin (Angiotensin converting enzyme inhibitors, Brown NJ. & Vaughan, DE., Circulation (1998) 97 1411–1420).

Protein turnover. The ability of the cell to degrade unwanted, damaged or foreign proteins is of great importance in the maintenance of the cell. Limited proteolysis of foreign proteins is also important in the antigen presentation process and therefore in an appropriate immune response to pathogens.

Post-translational modification. The proteolysis of certain proteins is key in their ability to perform their function in the cell. For example, the biosynthesis of the insulin receptor involves the cleavage of a large precursor to produce the subunits of the receptor complex (Biosynthesis and glycosylation of the insulin receptor, Hedo, J. A., Kahn, C. R., Hayashi, M., Yamada, K. M., Kasuga, M., Journal of Biological Chemistry (1983) 258 10020–10026). The assembly of the plant lectin concanavalin A (con A) also involves the proteolysis of a precursor protein and the religation of fragments in an altered order to generate the mature protein (Traffic and assembly of concanavalin A, Bowles, D. J. & Pappin, D. J., Trends in Biochemical Science (1988) 13 60–64).

A process coincident with other forms of post-translational modification. Proteolysis is an important feature of the processes leading to the addition of glycosylphosphatidylinositol (GPI) anchors to proteins and also in some fatty acylation reactions (such as farnesylation or geranylgeranylation).

Thus, proteolysis is an important post-translational modification of proteins and peptides which occurs both within and outside of the cell and can be an essential part of other forms of post-translational modification such as addition of a GPI anchor or some fatty acids. The ability to measure the cleavage of a protein or peptide at a specific site where that protein or peptide is also accessible for the addition of a prenyl moiety or a GPI anchor will allow the in vitro and in vivo study of processes for which the methods currently available are limited.

However, methods presently available for monitoring or detecting protease activity are not sufficiently sophisticated to be useful. Reporters are currently available to follow proteolysis where a peptide containing the cut site of the protease of interest has fluorophores at either end. Modification is followed by a change in the fluorescent output on cleavage of the peptide (causing physical separation of the fluorophores). Methods are available for monitoring both in vivo and in vitro proteolysis given the availability of various chemical fluorophores and quenchers and also a number of GFP variants which can be expressed in the cell (Compositions for the detection of proteases in biological samples and methods of use thereof, Komoriya, A. & Packard, B. S., WO96/13607; Tandem fluorescent protein constructs, Tsien, R. Y., Heim, R. & Cubitt, A., WO97/

28261). All such methods, however, rely on the use of a synthetic reporter which is typically not the natural substrate for the enzyme being assayed. Moreover, the flexibility of the prior art systems is limited.

SUMMARY OF TE INVENTION

According to a first aspect of the present invention, there is provided a polypeptide multimer comprising a first polypeptide and a second polypeptide, wherein a) at least one of the polypeptides is susceptible to protease digestion;

b) association of the polypeptides to form a multimer is detectable via a signal; and c) digestion of at least one polypeptide results in modulation of the association state of the multimer and modulation of the signal.

The invention accordingly provides a polypeptide multimer, or a constituent polypeptide thereof, which is susceptible to protease digestion such that digestion leads to dissociation of the constituent polypeptides, or a part thereof, from the multimer. The dissociation and association of the polypeptides in the multimer is in turn detectable, for example via a label (further described-below), or by monitoring of molecular weight, such as by surface plasmon resonance, or by measuring the molecular interactions of polypeptides through changes in emission or absorbance spectra of constituent parts thereof. For example, the association of the multimer is detectable through the interaction of labels placed on two or more polypeptides, which differs depending on whether the polypeptides are multimerised or not. For example, where the labels are fluorescent labels, fluorescence resonance energy transfer (FRET) is observable when the labels are in close proximity in a multimer. FRET is absent or otherwise modulated when the multimer dissociates.

"Modulation of the signal" refers to the capacity to either increase or decease a measurable signal by at least 10%, 15%, 20%, 25%, 50%, 100% or more; such increase or decrease is contingent on proteolytic cleavage of at least one polypeptide component of a multimer.

The multimer may be a homomultimer or a heteromultimer. In the former, the polypeptide monomers are substantially identical, whilst in the latter they differ. Preferably, the multimer is a heteromultimer. In the context of the present invention, a "multimer" may be a dimer, consisting of two monomers; however, it may optionally be a trimer, tetramer, pentamer or hexamer, composed of groups of three or more monomers, or dimers, trimers, etc. of constituent components which are themselves composed of individual monomer components. In all of these situations, the invention requires merely that the molecule (referred to as a "multimer") should be capable of moving between an associated and a dissociated state in response to digestion of a component thereof by a protease enzyme.

According to the invention, binding of a first polypeptide to a second polypeptide is dependent upon protease digestion, which digestion may occur on one or more polypeptides.

As referred to herein, a polypeptide is "susceptible to digestion by a protease" if it is available for cleavage by one or more protease enzymes in accordance with the present invention. Advantageously, the polypeptide is susceptible to digestion by a specific protease enzyme, and preferably only susceptible to digestion by a specific protease enzyme. This facilitates the reduction of non-specific or background proteolysis and the use of the invention to assay specific proteolytic events.

Advantageously, digestion preferably occurs at a protease cleavable site, which may be engineered into the one or more of the polypeptide(s)—an "engineered site"—or may be naturally present in one or more of the polypeptide(s)—a "natural site". However, it is also possible to design one or more polypeptide(s) such that they are potentially exposed to digestion by a protease which initially recognises a site which may be distal to the polypeptide itself—such as on a further polypeptide bound to a polypeptide according to the invention—and/or by an exoprotease enzyme which digests non-site specifically from the N or C terminus of the polypeptide.

The term "protease cleavable site" refers to an amino acid sequence which is recognised by (i.e., a recognition site for) a protease enzyme. It is contemplated that a site comprises a small number of amino acids, typically from 2 to 10, less often up to 30 amino acids, and further that a site comprises fewer than the total number of amino acids present in the polypeptide.

An engineered protease cleavable site suitable for digestion may be placed within a polypeptide of the invention at a position such that formation of a multimer between the isolated polypeptide and its binding partner is dependent upon the intactness of the site.

It is contemplated that the position at which an engineered site is to reside may initially be determined by random placement of the site within the polypeptide, followed by testing by methods described herein of the ability of the polypeptide to associate into a multimer with its intended binding partner(s), or not, depending upon the intactness or otherwise of the site. A pair of polypeptides, of which at least one comprises a site so placed that association of the polypeptides is dependent on cleavage at this site, is useful in the present invention.

As used herein, the term "polypeptide" refers to a polymer in which the monomers are amino acids and are joined together through peptide or disulphide bonds. "Polypeptide" refers to a full-length naturally-occurring amino acid chain or a fragment thereof, such as a selected region of the polypeptide that is of interest in a binding interaction, or a synthetic amino acid chain, or a combination thereof. "Fragment thereof" thus refers to an amino acid sequence that is a portion of a full-length polypeptide, between about 8 and about 500 amino acids in length, preferably about 8 to about 300, more preferably about 8 to about 200 amino acids, and even more preferably about 10 to about 50 or 100 amino acids in length. Additionally, amino acids other than naturally-occurring amino acids, for example β-alanine, phenyl glycine and homoarginine, may be included. Commonly-encountered amino acids which are not gene-encoded may also be used in the present invention. All of the amino acids used in the present invention may be either the D- or L—optical isomer. The D-isomers are preferred for use in a specific context, further described below. In addition, other peptidomimetics are also useful, e.g. in linker sequences of polypeptides of the present invention (see Spatola, 1983, in *Chemistry and Biochemistry of Amino Acids, Peptides and Proteins*, Weinstein, ed., Marcel Dekker, New York, p. 267).

"Naturally-occurring" as used herein, as applied to a polypeptide or polynucleotide, refers to the fact that the polypeptide or polynucleotide can be found in nature. One such example is a polypeptide or polynucleotide sequence that is present in an organism (including a virus) that can be isolated from a source in nature. Once the polypeptide is engineered as described herein it is no longer naturally occurring but is derived from a naturally occurring polypeptide.

"Polynucleotide" refers to a polymeric form of nucleotides of 2 up to 1,000 bases in length, or even more, either ribonucleotides or deoxyribonucleotides or a modified form of either type of nucleotide. The term includes single and double stranded forms of DNA. The term is synonymous with "oligonucleotide".

As used herein, the term "associates" or "binds" refers to polypeptides as described herein having a binding constant sufficiently strong to allow detection of binding by a detection means, such as FRET. Preferably, the polypeptides, when associated or bound, are in physical contact with each other and have a dissociation constant (Kd) of about 10 $\mu$M or lower. The contact region may include all or parts of the two molecules. Therefore, the terms "substantially dissociated" and "dissociated" or "substantially unbound" or "unbound" refer to the absence or loss of contact between such regions, such that the binding constant is reduced by an amount which produces a discernible change in a signal compared to the bound state, including a total absence or loss of contact, such that the proteins are completely separated, as well as a partial absence or loss of contact, so that the body of the proteins are no longer in close proximity to each other but may still be tethered together or otherwise loosely attached, and thus have a dissociation constant greater than 10 $\mu$M (Kd). In many cases, the Kd will be in the mM range. The terms "complex" and, particularly, "dimer", "trimer", "tetramer", "multimer" and "oligomer", as used herein, refer to the polypeptides, peptides, proteins, domains or subunits in the associated or bound state. More than one molecule of each of the two or more polypeptides may be present in a complex, dimer, multimer or oligomer according to the methods of the invention.

As used herein the term "modulation of the association state" refers to the ability of a protease enzyme, as defined above, to promote, prevent or reverse the association of at least two polypeptides, as defined above, by at least 10%, preferably by 25–50%, highly preferably by 75–90% and, most preferably, by 95–100% relative to the association observed in the absence of digestion by a protease enzyme under the same experimental conditions.

According to the experimental conditions, a monomer or multimer may change its association state by partially associating or dissociating without being either entirely reduced to the constituent monomer polypeptides or present exclusively in a single multimeric form. For example, a single polypeptide may dissociate from a trimer, leaving a polypeptide dimer. Moreover, cleavage of one of the monomers may occur such that the label is removed, and the signal generated on multimer formation thus modulated, but the monomer otherwise remains part of the multimer.

Alternatively, the association of polypeptides to form a multimer is inhibited by the presence of a modification which can itself be removed by proteolysis, thus allowing association of the polypeptides into the multimer. Preferably, the modification is of a residue of a coiled coil which is susceptible to cleavage from one of the polypeptides, such that the coiled coil is no longer able to form; the modification may, for example, be a phosphorylation of one of the residues. Cleavage of the coil such that the modified residue is removed leaves remaining coiled coils available for association.

The "detectable signal" referred to herein may be any detectable manifestation attributable to the presence of a label and will depend on the means selected for label detection. For example, in the event that the label is detected by FRET, a label will be present on at least two polypeptide components of the multimer such that association and dissociation thereof can be monitored by measurement of energy transfer between the labels. However, if the label is detected for example by fluorescence correlation spectroscopy (FCS), which relies on the measurement of the rate of diffusion of a label, only a single labelled polypeptide is required. In the case of FCS detection, the labelled polypeptide is advantageously very much smaller than the associated multimer. For example, the labelled polypeptide is preferably between 25 and 50% of the molecular weight of the multimer, advantageously 10 to 25%, and more preferably 1 to 10% or less.

The "label" according to the invention preferably comprises a light emitting detection means, and the light emitting detection means advantageously emits light of at least a fluorescent wavelength emission. It is preferred that the light emitting detection means comprises two different fluorophores or fluorescent tags or groups.

A "fluorescent tag" or "fluorescent group" refers to either a fluorophore or a fluorescent protein or fluorescent fragment thereof "Fluorescent protein" refers to any protein which fluoresces when excited with appropriate electromagnetic radiation. This includes proteins whose amino acid sequences are either natural or engineered.

It is additionally preferred that the fluorophores comprise fluorescein and tetramethylrhodamine or another suitable pair. In another preferred embodiment, the label comprises two different fluorescent proteins. It is preferred that fluorescent proteins comprise any protein selected from the group consisting of green fluorescent protein (GFP), blue fluorescent protein, red fluorescent protein and other engineered forms of GFP.

Preferably, the polypeptide comprises a cysteine or lysine amino acid through which the label is attached via a covalent bond.

Preferably, the measuring is performed by fluorescent resonance energy transfer (FRET), fluorescence anisotropy or fluorescence correlation spectroscopy.

It is preferred that the fluorescence emitting means comprise two different fluorophores, and particularly preferred that the fluorophores comprise fluorescein and tetramethylrhodamine or another suitable pair.

As used herein with regard to fluorescent labels for use in FRET, the term "appropriate combination" refers to a choice of reporter labels such that the emission wavelength spectrum of one (the "donor" moiety) is within the excitation wavelength spectrum of the other (the "acceptor" moiety).

The invention also encompasses a pair of polypeptides which associate to form a multimer, the pair comprising a first polypeptide comprising at least one binding domain, at least one site susceptible to proteolytic digestion, and a label, whereby the proteolytic digestion of at least one polypeptide is detectable via binding of the binding domain with a second polypeptide; and a second polypeptide which is capable of binding to the first polypeptide, wherein multimer formation is detectable via the label.

The invention additionally provides a method of screening for a candidate modulator of enzymatic activity of a protease, the method comprising mixing in an appropriate buffer an appropriate amount of a polypeptide susceptible to protease digestion, wherein the polypeptide binds to at least a second polypeptide, and wherein at least one polypeptide is suitably labelled with detection means for monitoring association/dissociation between the polypeptides; and a sample of material whose enzymatic activity is to be tested; and monitoring the digestion of the polypeptide.

Modulation of the association of the polypeptides to form a multimer is indicative of a modulation in the activity of the protease enzyme, and therefore of the activity of the candidate protease enzyme modulator.

As used herein, the term "sample" refers to a collection of inorganic, organic or biochemical molecules which is either found in nature (e.g., in a biological- or other specimen) or in an artificially-constructed grouping, such as agents which might be found and/or mixed in a laboratory. Such a sample may be either heterogeneous or homogeneous.

As used herein, the interchangeable terms "biological specimen" and "biological sample" refer to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). "Biological sample" further refers to a homogenate, lysate or extract prepared from a whole organism or a subset of its tissues, cells or component parts, or a fraction or portion thereof. Lastly, "biological sample" refers to a medium, such as a nutrient broth or gel in which an organism has been propagated, which contains cellular components, such as proteins or nucleic acid molecules.

As used herein, the term "organism" refers to all cellular life-forms, such as prokaryotes and eukaryotes, as well as non-cellular, nucleic acid-containing entities, such as bacteriophage and viruses.

It is highly preferred that a method of the methods described above comprises real-time observation of association of an isolated polypeptide and its binding partner or of an isolated pair of polypeptides.

As used herein in reference to monitoring, measurements or observations in assays of the invention, the term "real-time" refers to that which is performed contemporaneously with the monitored, measured or observed events and which yields as a result of the monitoring, measurement or observation to one who performs it simultaneously, or effectively so, with the occurrence of a monitored, measured or observed event. Thus, a "real time" assay or measurement contains not only the measured and quantitated result, such as fluorescence, but expresses this in real time, that is, in hours, minutes, seconds, milliseconds, nanoseconds, picoseconds, etc. Shorter times exceed the instrumentation capability; further, resolution is also limited by the folding and binding kinetics of polypeptides.

A variant of the present invention as described above involves the use of first and second polypeptide binding domains, which are located on the same polypeptide, in a method according to the invention. The polypeptide is configured such that binding between the domains results in spatial rearrangement of labels present on the polypeptide, such that a signal is induced or modulated.

In a further aspect, the present invention provides a method for monitoring the activity of a protease enzyme, comprising the steps of:
 a) providing a first binding domain having associated therewith a label, and a second binding domain, wherein
  i) at least one of the binding domains is susceptible to protease digestion; and
  ii) the first and second binding domains are capable of binding to each other such that a detectable signal is generated by the label, and digestion of one or both of the polypeptides by the protease enzyme results in modulation of the binding of the polypeptides to each other and therefore of the detectable signal;
 b) allowing the binding domains to bind to each other and induce a detectable signal;
 c) contacting the binding domains with a protease enzyme; and
 d) detecting modulation of the detectable signal as a result of the modulation of the binding of the binding domains.

Where more than one polypeptide is used, the polypeptides are capable of associating to form a multimer. Preferably the multimer is a dimer, trimer, or tetramer. Advantageously, it is a dimer. Preferably, the label is present on two or more polypeptide constituents of the multimer.

Where the binding domains are present on a single polypeptide, it is not necessary for a multimer to be formed.

Detection of the signal attributable to the label in the binding domains may be carried out according to the invention as set forth above.

A "binding domain", as used herein, is a polypeptide domain capable of mediating the binding of one polypeptide to a second polypeptide. Exemplary binding domains are described below, and include bZIP domains, coiled coil domains, SH2 domains and SH3 domains.

As used herein, the term "contacting" refers to the act of placing two reagents in such a relationship that they may potentially interact in order to produce a chemical or biological effect. Preferably, the process of contacting involves admixing the reagents at an appropriate concentration in solution or suspension, either in liquid or solid phases, or both, in an appropriate buffer.

As used herein, the term "appropriate buffer" refers to a medium which permits activity of the protease enzyme used in an assay of the invention, such as a low-ionic-strength buffer or other biocompatible solution (e.g., water, containing one or more of physiological salt, such as simple saline, and/or a weak buffer, such as Tris or phosphate, or others as described hereinbelow), a cell culture medium, of which many are known in the art, or a whole or fractionated cell lysate; provided that it is compatible with the binding of the components of the assay of the invention, and with the selected signal employed. For example, the buffer advantageously does not include agents which quench fluorescence, if the signal is a fluorescent signal. An "appropriate buffer" permits digestion of polypeptides according to the invention and, preferably, inhibits degradation and maintains biological activity of the reaction components. Inhibitors of degradation, such as nuclease inhibitors (e.g., DEPC) are well known.

As used herein, the term "appropriate concentration" refers to an amount of reagent (for example, a labelled polypeptide of the invention) which is sufficient for the intended reaction to proceed in a detectable manner. For instance, in the case of a labelled polypeptide, an appropriate concentration may be considered to be that concentration at which the label emits a signal within the detection limits of a measuring device used in an assay of the invention. Such an amount is great enough to permit detection of a signal, yet small enough that a change in signal emission is detectable (e.g., such that a signal is below the upper limit of the device).

Moreover, the invention relates to a method for detecting or monitoring the activity of a modulator of a protease enzyme, comprising the steps of:
 a) providing a first binding domain, and a second binding domain, wherein
  i) at least one of the binding domains is susceptible to protease digestion; and
  ii) the first and second binding domains are capable of binding to each other such that a detectable signal is generated by the label, and digestion of one or both of the polypeptides by the protease enzyme results in modulation of the binding of the binding domains to each other and therefore of the detectable signal;

b) allowing the binding domains to bind to each other and induce a detectable signal;

c) contacting the binding domains with a protease enzyme;

d) detecting modulation of the detectable signal as a result of the modulation of the binding of the binding domains to determine a reference signal modulation;

e) contacting the binding domains with a protease enzyme and a candidate modulator of the protease enzyme; and f) detecting modulation of the detectable signal as a result of the modulation of the binding of the binding domains, and comparing the modulation detected with the reference signal modulation.

A "reference signal modulation" is the amount by which a detectable signal is modulated, as defined above, in response to the activity of a protease enzyme in accordance with the invention. For example, therefore, the signal may be modulated, that is increased or decreased, by 10%, 15%, 20%, 25%, 50%, 100% or more. The reference signal modulation may be calculated at any time, and used as a standard value; it need not be recalculated every time the assay is performed. Comparison of detected signal modulation values with the reference signal modulation preferably manifest themselves as increases or decreases in the percentage modulation with respect to the reference value.

The assay permits the assessment of the activity of compounds, whether naturally-occurring or synthesised, to modulate the activity of a protease enzyme. It thus permits the use of the invention to detect or monitor processes which rely on protease activity or result in or from protease activity, such as post-translational modifications of proteins. The invention preferably relates to a method for detecting or monitoring fatty acylation of a protein, wherein the reaction includes a proteolytic event comprising the foregoing steps.

The term "modulator" thus refers to a chemical compound (naturally occurring or synthesised), such as a biological macromolecule (e.g., nucleic acid, protein, non-peptide, or organic molecule), or an extract made from biological materials such as bacteria, plants, fungi, or animal particularly mammalian) cells or tissues, or even an inorganic element or molecule. Modulators are evaluated for potential activity as inhibitors or activators (directly or indirectly) of a biological process or processes (e.g., agonist, partial antagonist, partial agonist, antagonist, antineoplastic agents, cytotoxic agents, inhibitors of neoplastic transformation or cell proliferation, cell proliferation-promoting agents, and the like) by inclusion in screening assays described herein. The activities (or activity) of a modulator may be known, unknown or partially-known. Such modulators can be screened using the methods described herein.

The term "candidate modulator" refers to a compound to be tested by one or more screening method(s) of the invention as a putative modulator. Usually, various predetermined concentrations are used for screening such as 0.01 $\mu$M, 0.1 $\mu$M, 1.0 $\mu$M, and 10.0 $\mu$M, as described more fully below. Test compound controls can include the measurement of a signal in the absence of the test compound or comparison to a compound known to modulate the target.

"Modulation" refers to the capacity to either increase or decease the proteolytic activity of a protease enzyme by at least 10%, 15%, 20%, 25%, 50%, 100% or more; such increase or decrease may be contingent on the occurrence of a specific event, such as activation of a signal transduction pathway, and/or may be manifest only in particular cell types.

In a still further aspect, the invention provides the use of a polypeptide multimer according to the preceding aspects of the invention for the detection or monitoring of a protease activity.

Other features and advantages of the invention ae found in the detailed description of the invention, and in the following claims.

DETAILED DESCRIPTION OF THE INVENTION

Figure 1:
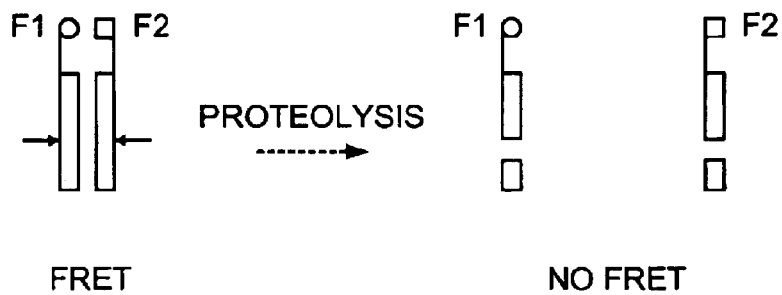
FIG. 1 is a diagrammatic representation of a homo-oligomeric assay of the invention in which each of the polypeptides comprises a protease cleavage site.

Generally, the nomenclature used herein and the laboratory procedures in cell culture, molecular genetics, and nucleic acid chemistry and hybridisation described below are those well known and commonly employed in the art. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., *Molecular Cloning: A Laboratory Manual* 2d ed. (1989) Cold Spring Harbor Laboratory Press, Cold Spring Harbor, N.Y., which is incorporated herein by reference) which are provided throughout this document. The nomenclature used herein and the laboratory procedures in analytical chemistry, organic synthetic chemistry, and pharmaceutical formulation described herein are those well known and commonly employed in the art. Standard techniques are used for chemical syntheses, chemical analyses, pharmaceutical formulation and delivery, and treatment of patients.

The present invention may be configured in a number of ways. Exemplary embodiments of the invention are set forth below.

Design and Construction of Polypeptides

Polypeptides useful in the present invention are capable of multimerising, either with similar or different polypeptides, to form a polypeptide multimer in accordance with the invention. Such polypeptides may be naturally-occurring polypeptides, modified naturally-occurring polypeptides, or artificial polypeptides. Naturally-occurring polypeptides may be isolated from natural sources or, preferably, synthesised by peptide synthesis or produced using recombinant DNA expression technology. Synthetic or partially synthetic polypeptides may be synthesised by peptide synthesis or using recombinant DNA technology and, if necessary, nucleic acid synthesis techniques. Various techniques for the synthesis of nucleic acids and peptides are known in the art and may be applied to the present invention.

In a preferred embodiment, labelled polypeptides may be produced via the expression of recombinant nucleic acid molecules comprising an in-frame fusion of sequences encoding a desired polypeptide and a fluorescent protein moiety either in vitro (e.g., using a cell-free transcription/ translation system, as described below, or instead using cultured cells transformed or transfected using methods well known in the art) or in vivo, for example in a transgenic animal including, but not limited to, insects, amphibians and mammals. A recombinant nucleic acid molecule of use in the invention may be constructed and expressed by molecular methods well known in the art, and may additionally comprise sequences including, but not limited to, those which encode a tag (e.g., a histidine tag) to enable easy purification, a secretion signal, a nuclear localisation signal or other primary sequence signal capable of targeting the construct to a particular cellular location, if it is so desired.

The use of heteromultimers is advantageous in several ways —unproductive label partnerships are outlawed; assays can be configured such that a number of modifications can be monitored using unique, modified polypeptides peculiar to each assay and one common polypeptide, which is important in the automation of assays; moreover, where only one polypeptide is susceptible to cleavage, only a single cleavage event is possible per multimer, which increases the output of the assay as unproductive cleavages are avoided.

The structural requirements for a polypeptide useful in the present invention may be defined as follows. Firstly, the polypeptide requires a binding site which will permit it to bind to other polypeptides to form a multimer. Polypeptides are known to be able to associate in a number of ways, and domains which mediate polypeptide association are also known. For example, the coiled coil domain is known to mediate protein—protein interactions, as are variants including both canonical and non-canonical coiled-coil repeat structures, such as leucine zipper domains, and non-coiled-coil domains such as SH2 domains and SH3 domains.

Table 5 sets forth a number of protein binding domains useful in the present invention.

TABLE 5

| Class | Sub-class | Partner 1 | Example positions for engineered sites | Partner 2 | Possible positions for engineered sites |
|---|---|---|---|---|---|
| INTRA-MOLECULAR | | PKC pseudo-RACK site□ Hemolin domains 1, 2 M63398 | | PKC RACK binding site□ Hemolin domains 3, 4 M63398 | |
| HOMO-OLIGOMER | | PKA RIIβ M31158 | 1–36 | PKA RIIβ M31158 | 1–36 |
| | | MetJ monomer M12869 | 20–29, 52–66 | MetJ monomer M12869 | 20–29, 52–66 |
| | | Phospholamban M60411 | 18–31 | Phospholamban M60411 | 18–31 |
| HETERO-OLIGOMER | SH2‡ | Src K03218 | 150–247 | RACK1 M24194 | |
| | | Src J00844 | 147–244 | AFAP110 L20303 | |
| | | RasGAP M23379 | 181–272, 351–441 | EphB2 L25890 (mouse) | juxta-membrane region, AF025304 (human) | including 604–613 (mouse) |
| | SH3 | ArgBP2 AF049884 | 436–484, 614–664 | Arg** | pro rich region 2 |
| | | CRKL X59656 | 123–296 | Abl 1 X16416 | 782–1019 |
| | PDZ | nNOS U17327 | 1–195 | PSD 95 U83192 | 138–294 |
| | | PTP-BL Z32740 | 1352–1450, 1756–1855 | RIL Y08361 | 249–330 (LIM domain) |
| | PH | RAC protein kinase β_ M77198 | 1–108 | PKC ζ_* | 1–250 |
| | | βARK X61157 | 556–670 | Gβγ_ω̄ | WD40 repeats 5 and 6 |
| | PTB φ | IRS 1 S62539 | 157–267 | ILA-R X52425 | 489–499 |
| | | Cbl X57110 | 1–357 | ZAP 70 L05148 | 284–299 |
| | WW | Nedd4 D42055 | 218–251, 375–408, 448–481, 500–533 | Amiloride-sensitive Na+ channel β subunit L36593 γ subunit L36592 | C-terminal P2 region |
| | AKAP | AKAP 79 M90359 | 388–409 | PKA RIIβ M31158 | 1–36 |
| | | AKAP 79 M90359 | 31–52 | PKC α, β1, β2 ζ | |
| | | AKAP 79 M90359 | 81–102 | Calcineurin (A subunit) M81483 | |
| | | Gravin U81607 | 1537–1563 | PKA RIIβ M31158 | 1–45 |
| | | Gravin U81607 | 265–556 | PKC β2^Å | |
| | RACK | RACK1 M24194 | | PKCβ1 X06318, M27545 | 186–198, 209–226 |
| | | b'COP X70476 | | PKCe X65293, S46030 | 2–145 |
| | YXDED | ZIP⁻ Y08355 | 41–105 | PKC ζ⁻ | 79–145 |

□Ron, D., Mochly-Rosen, D., Proceedings of the National Academy of Sciences USA 1995, 92 492–496.
‡The SH2 domain is modified such that the addition or removal of a phosphate group from a tyrosine residue is no longer a determinant of binding. This is achieved by thiophosphorylation of the Tyr residue in an in vitro assay to yield a permanently phosphorylated protein. Alternatively, it is possible to mimic phosphorylation by the mutation of the key Tyr residue to Glu or Asp.
**Wang, B., Golemis, E. A., Kruh G. D., Journal of Biological Chemistry 1997, 272 17542–17550
^Konishi, H., Kuroda, S., Kikkawa, U., Biochemical and Biophysical Research Communications 1994, 205 1770–1775.

TABLE 5-continued

| Class | Sub-class | Partner 1 | Example positions for engineered sites | Partner 2 | Possible positions for engineered sites |
|---|---|---|---|---|---|

ωFushman, D., Najmabadi-Haske, T., Cahill, S., Zheng, J., LeVine III, H., Cowburn, D., Journal of Biological Chemistry 1998, 273 2835–2843.
φAgain, the PTB domain is modified such that the addition or removal of a phosphate group from a tyrosine residue is no longer a determinant of binding. This is achieved by thiophosphorylation of the Tyr residue in an in vitro assay to yield a permanently phosphorylated protein. Alternatively, it is possible to mimic phosphorylation by the mutation of the key Tyr residue to Glu or Asp.
ζKlauck, T. M., Faux, M. C., Labudda, K., Langeberg, L. K., Jaken, S., Scott, J. D., Science 1996, 271 1589–92
ΛNauert, J. B., Klauck, T. M., Langeberg, L. K., Scott, J. D., Current Biology 1997, 7 52–62
⁻Puls, A., Schmidt, S., Grawe, F., Stabel, S., Proceedings of the National Academy of Sciences USA 1997, 94 6191–6196.

ZIP contains more than one protein binding motif (YXDED motif, ZZ zinc finger) and is known to bind to several proteins other than PKC ζ (including p62 and EBIAP) and also to self-associate (this self association is in competition with PKC ζ binding). These multiple interactions should be considered when designing an assay according to the present invention.

The coiled-coil domain is structurally conserved among many proteins that interact to form homo- or heterodimeric oligomers. The leucine zipper provides an example of one such protein transcriptional activator of a family of genes involved in the General Control of Nitrogen (GCN4) metabolism in *S. cerevisiae*. The protein is able to dimerise and bind promoter sequences containing the recognition sequence for GCN4, thereby activating transcription in times of nitrogen deprivation.

Coiled-coils are α-helical oligomers or bundles with between 1 and 5 polypeptide strands with the following characteristics: (i) a sequence hallmark of a predominance of hydrophobic residues (in particular alanine, isoleucine, leucine, methionine or valine) spaced 3 and 4 residues apart in the primary sequence which is repeated three or more times in near or exact succession (canonical heptad coiled-coil repeat, abbreviated to $(3, 4)_n$, where n=3 or greater). The hydrophobic residues are present at the 'a' and 'd' positions within a heptad when the amino acids are identified as positions a, b, c, d, e, f and g by order of sequence. In addition, spacing of hydrophobic residues in patterns of 3, 4, 4 and 3, 4, 3 (hendecad repeat) have recently been reported (Hicks et al., 1997, *Folding and Design*, 2: 149–158) and are compatible with the coiled-coil structure. (ii) In structural terms coiled-coil helical bundles have between 2 and 5 helices which are offset at roughly 20° to adjacent strands with the hydrophobic sidechains interdigitating in the interface between helices in what is termed the "knobs into holes" packing (Crick, 1953, *Acta Crystallogr*, 6: 689–697). Natural and non-natural coiled-coils can have parallel and/or antiparallel helices. Both homotypic (multiple strands of identical sequence) and heterotypic bundles have been described.

Leucine zipper sequences conform to the coiled-coil rules above and typically have leucine residues at the 'd' position of the canonical heptad repeat. These leucine residues represent a single face of the helix. Interdigitating with these leucine residues are other hydrophobic amino acids, frequently valine, isoleucine or leucine residues. The combination of these residues forms a continuous hydrophobic face which associates with an equivalent region in an associating subunit. Alternatively the hydrophobic face can be discontinuous due to interruptions in the heptad repeat sequence. This, however, does not interfere with the ability of these coiled-coils to interact. The stability of the dimer thus formed is conferred by the hydrophobic interactions between the leucine residues and the interdigitating hydrophobic residues. Hydrogen bonds that form between residues present on the two interacting helices, particularly at the e and g positions, also contribute to the stability of the dimer. The coiled-coil domain of GCN4 has been shown to dimerise as an isolated peptide (Gonzalez et al., 1996, Nature Structural Biology, 3: 1011–1018).

Examples of naturally-occurring coiled-coils are as follows:
Coiled-oil class and example:

fgabcdefgabcdefgabcdefgabcdefgabcdefgabcdeg
Parallel two-stranded tropomyosin
TMPA_RABIT, 10–279 (270)
(J. BIOL. CHEM. 253, 1137–1148, 1978)
dystrophin     ILISLESEERGELERILADLEEENRNLQAEYDRLKQQHEHK
SWISS PROT:P11532 (HUMAN)     (SEQ ID NO:3)
(Trends Biol. Sci., 20, 133–135, 1995)
GCN4*     MKQLEDKVEELLSKNYHLENEVARLKKLVGER
GCN4_YEAST, 250–281 (32)     (SEQ ID NO:4)
(Proc. Natl. Acad. Sci. U.S.A., 81, 6442–6446, 1982)
cFOS*     TDTLQAETDQLEDEKSALQTEIANLLKEKEKLEFILAAH
FOS_HUMAN, 162–199 (39)     (SEQ ID NO:5)
(Proc. Natl. Acad. Sci. U.S.A., 80: 3183–3187, 198)
cJUN*     IARLEEKVKTLKAQNSELASTANMLREQVAQLKQKVMNH
AP1_HUMAN, 277–315 (39)     (SEQ ID NO:6)
(Proc. Natl. Acad. Sci. U.S.A., 85: 9148–9152, 1988
antiparallel two-stranded Seryl-tRNA synthetase, *E. coli*\*     VDKLGALEERRKVLQVKTENLQAERNSRSKSIGQAKAR
SYS_ECOLI, 27–64 (38)     (SEQ ID NO:7)
NUCLEIC ACIDS RES., 15,     EPLRLEVNKLGEELDAAKAELDALQAEIRDIA
1005–1017, 1987     (SEQ ID NO:8)
SYS_ECOLI, 69–100 (32)
Seryl-tRNA synthetase,     DLEALLALDREVQELKKRLQEVQTERNQVAKRV
Thermus thermophilus*     (SEQ ID NO:9)

-continued

| | |
|---|---|
| SYS_THERM, 26–58 (33)<br>(Science, 263: 1404–141)<br>SYS_THERM, 67–98 (32)<br>Transcript cleavage factor GreA*<br>GREA_ECOLI, 8–37 (30)<br>(Nature, 373: 636–640, 1995)<br>GREA_ECOLI, 46–71 (26)<br>Parallel three-stranded | EALIARGKALGEEAKRLEEALREKEARLEALL<br>(SEQ ID NO:10)<br><br><br>LRGAEKLREELDFLKSvFRPEIIAAIAEAR<br>(SEQ ID NO:11)<br>AEYHAAREQQGFCEGRIKDIEAKLSN<br>(SEQ ID NO:12) |
| GCN4 Zip mutant pII*<br>GCN4 Zip mutant pII*<br>(Nature, 371: 80–83)<br>Antiparallel three-stranded | MKQIEDKIEEILSKIYHIENEIARIKKLIGER<br>(SEQ ID NO:13) |
| synthetic peptide coil-Ser*<br>(Science, 259: 1288–1293)<br>Parallel four-stranded | EWEALEKKLAALESKLQALEKKLEALEHG<br>(SEQ ID NO:14) |
| GCN4 Zip mutant pLI*<br>(Nature, 371: 80–83)<br>Antiparallel four-stranded | MKQIEDKLEEILSKLYHIENELARIKKLLGER<br>(SEQ ID NO:15) |
| Repressor of primer ROP*<br>ROP_ECOLI, 4–28 (25)<br>(Proc. Natl. Acad. Sci. U.S.A.,<br>79: 6313–6317 1982)<br>ROP_ECOLI, 32–55 (24)<br>Parallel five-stranded | QEKTALNMARFIRSQILTLLEKLNE<br>(SEQ ID NO:16)<br>DEQADICESLHDHADELYRSCLAR<br>(SEQ ID NO:17) |
| phospholamban<br>PPLA_HUMAN, 37–52 (16)<br>(JBC 271, 5941–5946, 1996) | LILICLLLICIIVMLL<br>(SEQ ID NO:18) |

The binding domains may be similar or different, i.e. homomultimeric or heteromultimeric. The rules for the design of hetero-multimeric coiled coils are well detailed in the literature (including Peptide 'Velcro': design of a heterodimeric coiled coil, O'Shea, E. K., Lumb, K. J. & Kim, P. S., Current Biology (1993) 3 658–667; A designed heterotrimeric coiled coil, Nautiyal, S., Woolfson, D. N., King, D. S. & Alber T., Biochemistry (1995) 34 11645–11651; A buried polar interaction imparts structural uniqueness in a designed heterodimeric coiled coil, Lumb, K. J. & Kim P. S., Biochemistry (1995) 34 8642–8648). The use of a 'designer' coiled coil has benefit in providing control over the potential modification sites present other than those inserted to monitor the reaction of interest.

Of course, polypeptides may also associate via interactions, not necessarily involving canonical domains such as coiled-coils, which may be specific to the polypeptides in question.

Secondly, one or more polypeptides in each multimer may comprise a label. Suitable fluorescent labels include fluorophores and fluorescent proteins. As used herein, the terms "fluorophore" and "fluorochrome" refer interchangeably to a molecule which is capable of absorbing energy at a wavelength range and releasing energy at a wavelength range other than the absorbance range. The term "excitation wavelength" refers to the range of wavelengths at which a fluorophore absorbs energy. The term "emission wavelength" refers to the range of wavelength that the fluorophore releases energy or fluoresces.

A non-limiting list of chemical fluorophores of use in the invention, along with their excitation and emission wavelengths, is presented in Table 1.

TABLE 1

| Fluorophore | Excitation (nm) | Emission (nm) | Colour |
|---|---|---|---|
| PKH2 | 490 | 504 | green |
| PKH67 | 490 | 502 | green |
| Fluorescein (FITC) | 495 | 525 | green |
| Hoechst 33258 | 360 | 470 | blue |
| R-Phycoerythrin (PE) | 488 | 578 | orange-red |
| Rhodamine (TRITC) | 552 | 570 | red |
| Quantum RedÒ | 488 | 670 | red |
| PKH26 | 551 | 567 | red |
| TEXAS RED ™ | 596 | 620 | red |
| Cy3 (Indodicarbocyanine-3) | 552 | 570 | red |

Examples of fluorescent proteins which vary among themselves in excitation and emission maxima are listed in Table 1 of WO 97/28261 (incorporated herein by reference). These (each followed by [excitation max./emission max.] wavelengths expressed in nanometers) include wild-type Green Fluorescent Protein [395(475)/508] and the cloned mutant of Green Fluorescent Protein variants P4 [383/447], P4–3 [381/445], W7 [433(453)/475(501)], W2 [432(453)/480], S65T [489/511], P4-1 [504(396)/480], S65A [471/504)]S65C [479/507], S65L [484/510], Y66F [360/442], Y66W [458/480], I0c [513/527], WIB [432(453)/476(503)], Emerald [487/508] and Sapphire [395/511]. This list is not exhaustive of fluorescent proteins known in the art; additional examples are found in the Genbank and SwissProt public databases.

A number of parameters of fluorescence output are envisaged including
1) measuring fluorescence emitted at the emission wavelength of the acceptor (A) and donor (D) and determining the extent of energy transfer by the ratio of their emission amplitudes;

2) measuring the fluorescence lifetime of D;
3) measuring the rate of photobleaching of D;
4) measuring the anistropy of D and/or A; or
5) measuring the Stokes shift monomer:eximer fluorescence.

Other labels may be used, however, depending on the detection method employed to monitor the signal generated by the label. Labels may be attached in a number of ways, such as by direct labelling at suitable amino acids, such as cysteines or lysines, with chemical labels, or by fusion with a polypeptide-label such as a fluorescent polypeptide. Techniques for labelling polypeptides are generally known in the art and may be applied to the present invention.

The invention may be configured to exploit a number of non-fluorescent labels. In a first embodiment, the polypeptide multimer is an enzyme which is capable of participating in an enzyme-substrate reaction which has a detectable endpoint. The enzyme may be cleaved into two or more components, such that upon multimer formation the components reassemble to form a functional enzyme. Enzyme function may be assessed by a number of methods, including scintillation and photospectroscopy.

Cleavage of one or more polypeptides according to the invention is required to preclude multimer formation and enzyme component assembly, thus reducing enzyme activity.

In a second embodiment, an enzyme is used together with a modulator of enzyme activity, such as an inhibitor or a cofactor. Binding of the enzyme and its inhibitor or cofactor results in modulation of enzymatic activity, which is detectable by conventional means.

In a third embodiment, the invention is configured as a two-hybrid assay (Fields & Song, (1989), Nature 340, 245–6), in which two components of a transcription factor are used as polypeptides according to the invention. Assembly of the transcription factor results in activation of a transcription unit, with a resultant biological signal; a preferred biological signal is luciferase expression, which is easily assessed. Cleavage of one or more of the components results in downregulation of the transcription unit and thus loss of signal.

In any of the foregoing embodiments, assembly of the enzyme or transcription factor components may be spontaneous, such that the enzyme or transcription factor components are themselves the polypeptides according to the invention. Furthermore, it may be dependent upon the association of associated binding domains, such that the enzyme and transcription factor components are effectively labels according to the present invention. A two-hybrid type of assay is preferably configured in this manner.

Thirdly, one or more of the polypeptides in each multimer according to the invention must be susceptible to digestion by a protease enzyme. As noted above, susceptibility to digestion indicates that the polypeptide may be subjected to proteolytic degradation under the appropriate conditions, which in a preferred embodiment means that the polypeptide is cleaved by a protease at a recognition site for the protease enzyme. Alternatively, however, the polypeptide may be susceptible to digestion by an exoprotease, from the N or C terminus. Peptides may be rendered susceptible to protease digestion by inclusion within the peptide sequence of a recognition site for a protease. This may be performed using peptide synthesis techniques as described above.

Polypeptides according to the invention should be constructed such that the protease cleavable site is positioned such that cleavage thereof disrupts binding of the polypeptide in the context of the multimer. Thus, polypeptides which have been subjected to protease cleavage should dissociate from the multimer. Preferably, the protease does not cleave the polypeptide in such a manner that the label becomes detached therefrom without the binding abilities thereof being disrupted. Location of the protease cleavage site may be determined empirically. As a guide, however, the site should be placed within or proximal to the binding domain which is responsible for the multimerisation of the polypeptide.

In the case of coiled coil binding domains, Lumb et al (Subdomain folding of the coiled coil leucine zipper from the bZIP transcriptional activator GCN4, Lumb, K. J., Carr, C. M. & Kim, P. S., Biochemistry (1994) 33 7361–7367) teach that the loss of ten residues from the N-terminus or seven from the N- and six from the C-terminus is sufficient to destabilise the coiled coil peptide sequence known as GCN4-p1 (Evidence that the leucine zipper is a coiled coil, O'Shea, E. K., Rutkiowski, R. & Kim, P. S. (1989) Science 243 538–542). Su et al provide data indicating that there is a sharp decrease in the stability of a designed coiled coil with a decrease in chain length from 23 to 19 residues (Su, J. Y., Hodges, R. S. & Kay, C. M., Biochemistry (1994) 33 15501–15510). Accordingly, cleavage sites may positioned such that the coiled coil is disrupted to an extent that it is no longer capable of directing multimerisation.

The cleavage sites of a number of proteases are known in the art, and set forth in Table 2.

TABLE 2

| Protease | Cut Site(s) | Possible/Proven Role |
|---|---|---|
| Aminopeptidase M | Hydrolysis from free N-terminus | digestion |
| Carboxypeptidase P | Hydrolysis from C-terminus | digestion |
| Carboxypeptidase Y | Hydrolysis from C-terminus | digestion |
| Caspase 1, 4, 5 | W/LEHD-X[#] (SEQ ID NO:19) | mediator of apoptosis |
| Caspase 2, 3, 7 | DEXD-X[#] (SEQ ID NO:20) | mediator of apoptosis |
| Caspase 6, 8, 9 | L/VEXD-X[#] (SEQ ID NO:21) | mediator of apoptosis |
| Chymotrypsin | Y-X, F-X, T-X, (L-X, M-X, A-X, E-X) | digestion |
| Factor Xa | IEGR-X (SEQ ID NO:22) | blood clotting cascade |
| Pepsin | F-Z, M-Z, L-Z, W-Z (where Z is a hydrophobic residue) but will cleave others | digestion |
| TEV | E(N)XYXQ-S/G[−] (SEQ ID NO:23) | polyprotein processing/as a reagent |
| Thrombin | R-X | blood clotting cascade |
| Trypsin | R-X, K-X | digestion |

[#]Ideal cut sites identified by Thornberry et al in A combinatorial approach defines specificities of members of the caspase family and granzyme B, Journal of Biological Chemistry 272 17907–17911.
[−]Release of proteins and peptides from fusion proteins using a recombinant plant virus proteinase, Parks, T. D., Keuther, K. K., Howard, E. D., Johnston, S. A. & Dougherty, W. G., Analytical Biochemistry (1994) 216 413–417; Life Technologies Ltd.

The foregoing, or other, sites may be engineered into or close to the binding domains of polypeptides according to the invention.

In a preferred aspect of the present invention, it is desirable to engineer specificity into the polypeptide, such that it is digested only by the desired protease and only at the intended protease cleavable site. This may be achieved, for example, by the use of D-isomers of amino acids in the construction of the polypeptide. D-amino acids are resistant to protease digestion, and a polypeptide constructed of D-amino acids will withstand proteolytic attack. Moreover, use of D-amino acids does not interfere with the protein—protein interactions involved in multimerisation, such as the interaction of protein binding domains, especially coiled-coil domains, provided that D amino acids are employed in both members of a binding pair.

In order to allow digestion by the intended protease enzyme, the D-amino acid constructions of the polypeptides of the invention contain one or more parts constructed of L-amino acids, or otherwise rendered susceptible to proteolytic digestion. For example, coiled coils constructed of D-amino acids preferably comprise inserts, constructed wholly or partly of L-amino acids, which contain the protease cleavage site. The L-amino acid insert may be of any size, and may be positioned between coiled coil repeats, or between residues of the coiled coil. Preferred are insertions between residues b–c, e–f and f–g. The insert is covalently attached to the coiled coil, through a peptide linkage to the backbone or through a sidechain.

The insert may comprise only a cleavage site, or an entire polypeptide. Functionally, the insert is sufficiently flexible to permit the coiled coil to bind to its target efficiently when the insert is intact. For example, the insert may comprise a flexible linker, such as a gly—gly linker. Molecules comprising D-amino acids are advantageously employed in in vitro assays.

Inserts as described above may be employed in D-amino acid coiled coils, in conventional L-amino acid coiled coils, or in coiled coils which are partially D and partially L in construction. Foe example, a coiled coil may be constructed such that it consist of L-amino acids on one side of the insert, and D-amino acids on the other side thereof.

Generation of a Detectable Signal

Depending on the embodiment in question, a signal useful in the present invention may be generated by a number of different labels. Preferred are fluorescent labels, and particularly preferred are fluorescent labels which participate in energy transfer (FRET).

FRET is detectable when two fluorescent labels which fluoresce at different frequencies are sufficiently close to each other that energy is able to be transferred from one label to the other. FRET is widely known in the art (for a review, see Matyus, 1992, *J. Photochem. Photobiol. B: Biol.*, 12: 323–337, which is herein incorporated by reference). FRET is a radiationless process in which energy is transferred from an excited donor molecule to an acceptor molecule; the efficiency of this transfer is dependent upon the distance between the donor and acceptor molecules, as described below. Since the rate of energy transfer is inversely proportional to the sixth power of the distance between the donor and acceptor; the energy transfer efficiency is extremely sensitive to distance changes. Energy transfer is said to occur with detectable efficiency in the 1–10 nm distance range, but is typically 4–6 mm for favourable pairs of donor and acceptor.

Radiationless energy transfer is based on the biophysical properties of fluorophores. These principles are reviewed elsewhere (Lakowicz, 1983, *Principles of Fluorescence Spectroscopy*, Plenum Press, New York; Jovin and Jovin, 1989, *Cell Structure and Function by Microspectrofluorometry*, eds. E. Kohen and J. G. Hirschberg, Academic Press, both of which are incorporated herein by reference). Briefly, a fluorophore absorbs light energy at a characteristic wavelength. This wavelength is also known as the excitation wavelength. The energy absorbed by a fluorochrome is subsequently released through various pathways, one being emission of photons to produce fluorescence. The wavelength of light being emitted is known as the emission wavelength and is an inherent characteristic of a particular fluorophore. Radiationless energy transfer is the quantum-mechanical process by which the energy of the excited state of one fluorophore is transferred without actual photon emission to a second fluorophore. That energy may then be subsequently released at the emission wavelength of the second fluorophore. The first fluorophore is generally termed the donor (D) and has an excited state of higher energy than that of the second fluorophore, termed the acceptor (A). The essential features of the process are that the emission spectrum of the donor overlap with the excitation spectrum of the acceptor, and that the donor and acceptor be sufficiently close. The distance over which radiationless energy transfer is effective depends on many factors including the fluorescence quantum efficiency of the donor, the extinction coefficient of the acceptor, the degree of overlap of their respective spectra, the refractive index of the medium, and the relative orientation of the transition moments of the two fluorophores. In addition to having an optimum emission range overlapping the excitation wavelength of the other fluorophore, the distance between D and A must be sufficiently small to allow the radiationless transfer of energy between the fluorophores.

FRET may be performed either in vivo or in vitro. Proteins are labelled either in vivo or in vitro by methods known in the art. According to the invention, two coiled-coil domains comprised either by the same or by different polypeptide molecules are differentially labelled, one with a donor and the other with an acceptor moiety, and differences in fluorescence between a test assay, comprising a protein modifying enzyme, and a control, in which the modifying enzyme is absent, are measured using a fluorimeter or laser-scanning microscope. It will be apparent to those skilled in the art that excitation/detection means can be augmented by the incorporation of photomultiplier means to enhance detection sensitivity. The differential labels may comprise either two different fluorescent moieties (e.g., fluorescent proteins as described below or the fluorophores rhodamine, fluorescein, SPQ, and others as are known in the art) or a fluorescent moiety and a molecule known to quench its signal.

In a FRET assay of the invention, the fluorescent labels are chosen such that the excitation spectrum of one of the labels (the acceptor label) overlaps with the emission spectrum of the excited fluorescent label (the donor label). The donor label is excited by light of appropriate intensity within the donor's excitation spectrum. The donor then emits some of the absorbed energy as fluorescent light and dissipates some of the energy by FRET to the acceptor fluorescent label. The fluorescent energy it produces is quenched by the acceptor fluorescent label. FRET can be manifested as a reduction in the intensity of the fluorescent signal from the donor, reduction in the lifetime of its excited state, and re-emission of fluorescent light at the longer wavelengths (lower energies) characteristic of the acceptor. When the donor and acceptor labels become spatially separated, FRET is diminished or eliminated.

One can take advantage of the FRET exhibited by two polypeptides labelled with different fluorescent labels, wherein one polypeptide is linked to a donor and another to an acceptor label, in monitoring proteolytic digestion according to the present invention. Two distinct polypeptides each comprising a coiled-coil may be differentially labelled with the donor and acceptor fluorescent protein moieties, respectively.

The means by which polypeptides are assayed for association using fluorescent protein moiety labels according to the invention may be briefly summarised as follows:

Of two polypeptides which associate into a multimer according to the present invention, one is labelled with a green fluorescent protein, while the other is preferably labelled with a red or, alternatively, a blue fluorescent protein. Useful donor:acceptor pairs of fluorescent proteins (see WO 97/28261) include, but are not limited to:

Donor: S72A, K79R, Y145F, M153A and T203I (excitation 395 nm; emission 511)

Acceptor: S659, S72A, K79R and T203Y (wavelengths not noted), or T203Y/S65G, V68L, Q69K or S72A (excitation 515 nm; emission 527 nm).

An example of a blue:green pairing is P4-3 (shown in Table 1 of WO 97/28261) as the donor moiety and S65C (also of Table 1 of WO 97/28261) as the acceptor moiety. The polypeptides comprising coiled-coils are exposed to light at, for example, 368 nm, a wavelength that is near the excitation maximum of P4-3. This wavelength excites S65C only minimally. Upon excitation, some portion of the energy absorbed by the blue fluorescent protein moiety is transferred to the acceptor moiety through FRET if the two polypeptides comprising coiled-coils are in close association. As a result of this quenching, the blue fluorescent light emitted by the blue fluorescent protein is less bright than would be expected if the blue fluorescent protein existed in isolation. The acceptor moiety (S65C) may re-emit the energy at longer wavelength, in this case, green fluorescent light.

After proteolytic degradation, the polypeptides physically separate, accordingly inhibiting FRET. Such a system is useful to monitor the activity of proteolytic enzymes that cleave polypeptides to which the fluorescent labels are fused as well as the activity of modulators or candidate modulators of those enzymes.

In particular, the invention contemplates assays in which the amount or activity of a protease in a sample is determined by contacting the sample with a pair of polypeptides differentially labelled with fluorescent proteins, as described above, and measuring changes in fluorescence of the donor moiety, the acceptor moiety or the relative fluorescence of both. Fusion proteins, as described above, can be used for, among other things, monitoring the activity of a protease enzyme inside the cell that expresses two different recombinant constructs.

Advantages of fluorescent polypeptides constructed as fusions with fluorescent proteins include the greater extinction coefficient and quantum yield of many of these proteins compared with those of the Edans fluorophore. Also, the acceptor in such a construct or pair of constructs is, itself, a fluorophore rather than a non-fluorescent quencher like Dabcyl. Thus, the enzyme's substrate, i.e., the unmodified polypeptide of the construct(s) and products (i.e., the polypeptides after digestion) are both fluorescent but with different fluorescent characteristics.

In particular, the substrate and modified products exhibit different ratios between the amount of light emitted by the donor and acceptor labels. Therefore, the ratio between the two fluorescences measures the degree of conversion of substrate to products, independent of the absolute amount of either, the optical thickness of the sample, the brightness of the excitation lamp, the sensitivity of the detector, etc. Furthermore, Aequorea-derived or related fluorescent protein moieties tend to be protease resistant. Therefore, they are likely to retain their fluorescent properties throughout the course of an experiment.

Additional embodiments of the present invention are not dependent on FRET. For example the invention can make use of fluorescence correlation spectroscopy (FCS), which relies on the measurement of the rate of diffusion of a label (see Elson & Magde, (1974) Biopolymers 13:1–27; Rigler et al., (1992) in *Fluorescence Spectroscopy New Methods and Applications*, Springer Verlag, pp.13–24; Eigen & Rigler, (1994) PNAS (ISA) 91:5740–5747; Kinjo & Rigler, (1995) NAR 23:1795–1799).

In FCS, a focused laser beam illuminates a very small volume of solution, of the order of $10^{-15}$l, which at any given point in time contains only one molecule of the many under analysis. The diffusion of single molecules through the illuminated volume, over time, results in bursts of fluorescent light as the labels of the molecules are excited by the laser. Each individual burst, resulting from a single molecule, can be registered.

A labelled polypeptide will diffuse at a slower rate if it is large than if it is small. Thus, multimerised polypeptides will display slow diffusion rates, resulting in a lower number of fluorescent bursts in any given timeframe, whilst labelled polypeptides which are not multimerised or which have dissociated from a multimer will diffuse more rapidly. Binding of polypeptides according to the invention can be calculated directly from the diffusion rates through the illuminated volume.

Where FCS is employed, rather than FRET, it is not necessary to label more than one polypeptide. Preferably, a single polypeptide member of the multimer is labelled. The labelled polypeptide dissociates from the multimer as a result of protease digestion, thus altering the FCS reading for the fluorescent label.

A further detection technique which may be employed in the method of the present invention is the measurement of time-dependent decay of fluorescence anisotropy. This is described, for example, in Lacowicz (1983) *Principles of Fluorescence Spectroscopy*, Plenum Press, New York, incorporated herein by reference. See, for example, page 167.

Fluorescence anisotropy relies on the measurement of the rotation of fluorescent groups. Larger multimers of polypeptides rotate more slowly than monomers, allowing the formation of multimers to be monitored.

Protease Digestion

Digestion of polypeptides according to the invention with proteolytic enzymes may be carried out either in vivo or in vitro, according to techniques and procedures known in the art. Thus, appropriate amounts of polypeptides according to the invention are incubated in appropriate conditions, for example with an appropriate buffer.

As used herein, the term "appropriate buffer" refers to a medium which permits activity of the protease enzyme used in an assay of the invention, and is typically a low-ionic-strength buffer or other biocompatible solution (e.g., water, containing one or more of physiological salt, such as simple saline, and/or a weak buffer, such as Tris or phosphate, or others as described hereinbelow), a cell culture medium, of which many are known in the art, or a whole or fractionated cell lysate. An "appropriate buffer" permits digestion of polypeptides according to the invention and, preferably, inhibits degradation and maintains biological activity or the reaction components. Inhibitors of degradation, such as nuclease inhibitors (e.g., DEPC) are well known in the art. Lastly, an appropriate buffer may comprise a stabilising substance such as glycerol, sucrose or polyethylene glycol.

As used herein, the term "appropriate amounts of polypeptides" refers to an amount of labelled polypeptides of the invention which emit a signal within the detection limits of a measuring device used in an assay of the invention. Such an amount is great enough to permit detection of a signal, yet small enough that a change in signal emission is detectable (e.g., such that a signal is below the upper limit of the device).

Configuration of the Invention Using a Homomultimer Comprising a Protease Cleavage Site In one embodiment of the present invention, the assay may be configured to use a homomultimer of polypeptides, which are cleavable by a protease at a specific protease cleavable site.

This assay requires the formation of an oligomer of binding partners containing a proteolytic site or with a proteolytic site engineered therein which are labelled with fluorophores appropriate for FRET (or some other appropriate means of detection). The coiled coil provides a good example of such an oligomer. The sequence of the coiled coil part of the peptides in this reporter is advantageously short, such that it contains at least two heptad structures and preferably about 4 or 5 heptads. Within this heptad structure an amino acid sequence recognised as a cleavage site for a protease is included. Cleavage of the peptide by the protease will reduce the length of the continuous coiled coil sequence, and destabilise oligomer formation. The fluorophores (F1, F2; where F1 is the donor fluorophore and F2 the acceptor) should be positioned such that they are covalently attached to separate peptides in the oligomeric complex at positions which are close in space in this complex but are not attached to a residue which prevents enzyme processing of the substrate.

An assay based on a homo-oligomeric assembly of peptides is represented in FIG. 1.

Configuration of the Invention using a Heteromultimer Comprising a Protease Cleavage Site The assay may, however, also be configured as a heteromultimeric assay in which one or more of the polypeptides comprises a protease cleavage site.

Figure 2:
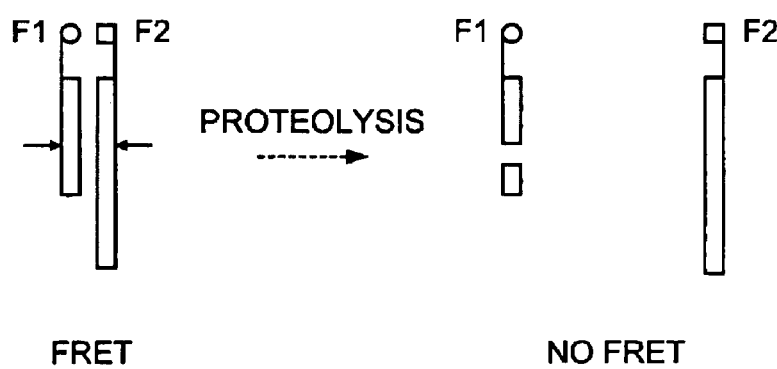
FIG. 2 is a diagrammatic representation of a heteromultimeric assay of the invention in which one or more of the polypeptides comprises a protease site.

Clearly, the assays may be modified with respect to the diagram in FIG. 2 in order to permit proteolytic degradation of more than one polypeptide in the multimer. However, one of the advantages of heteromultimeric assays is that only a single polypeptide is digested.

Figure 3:
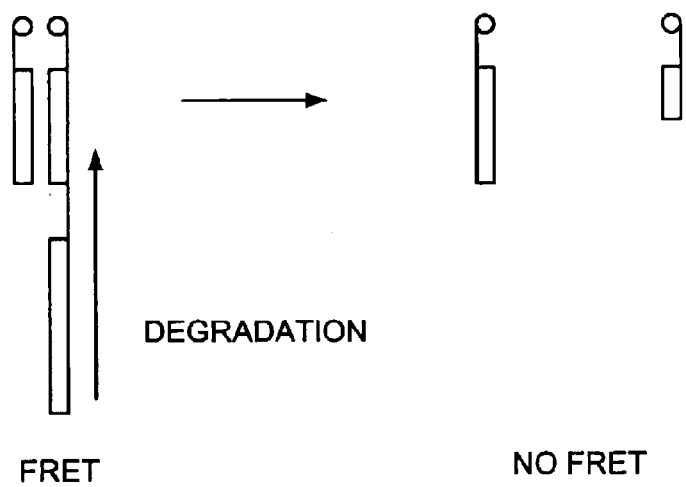
FIG. 3 is a diagrammatic representation of a multimeric assay of the invention in which one of the polypeptides is produced as a fusion protein with an additional polypeptide, and assayed for proteolytic degradation.

Configuration of the Invention Using Heteromultimer Susceptible to Proteolytic Degradation The invention may be configured to monitor the degradation of polypeptides, especially naturally-occurring polypeptides, as a result of proteolytic degradation. For instance, a polypeptide may be produced as a fusion with a further polypeptide which is to be assayed for proteolytic degradation. Protease enzymes which degrade the further polypeptide will also degrade the polypeptide of the invention, giving rise to multimer dissociation (FIG. 3).

Since the multimer is, in the embodiment, potentially much larger than the labelled dissociated monomer, the use of detection techniques reliant on label diffusion such as FCS is facilitated. Moreover, the use of single labelled polypeptides, in conjunction with FCS detection, is made possible.

Configuration of a Single-Polypeptide Binding Domains

Single-polypeptide reagents may be configured in a number of ways, depending on the location of the labels with respect to the binding domains on the polypeptide, In a first example (FIG. 4), the labels are positioned N- and C-terminal to the respective binding domains.

Figure 4:
FIG. 4 is a diagrammatic representation of a single-polypeptide reagent useful according to the invention.
Figure 4:
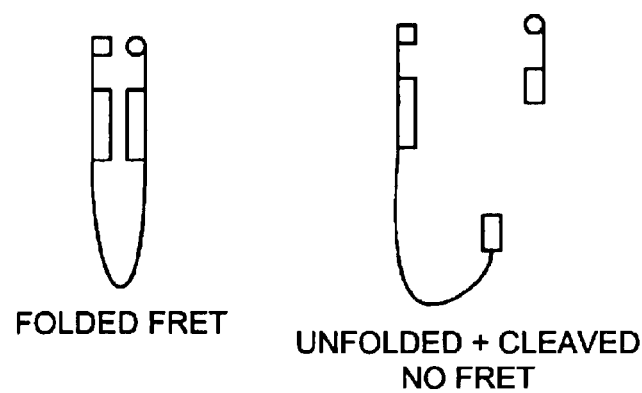

Unfolded polypeptide molecule—no FRET.
Folded molecule—FRET between labels.
Cleavage of one binding domain leads to unfolding of the molecule and loss of FRET (FIG. 4).

Figure 5:
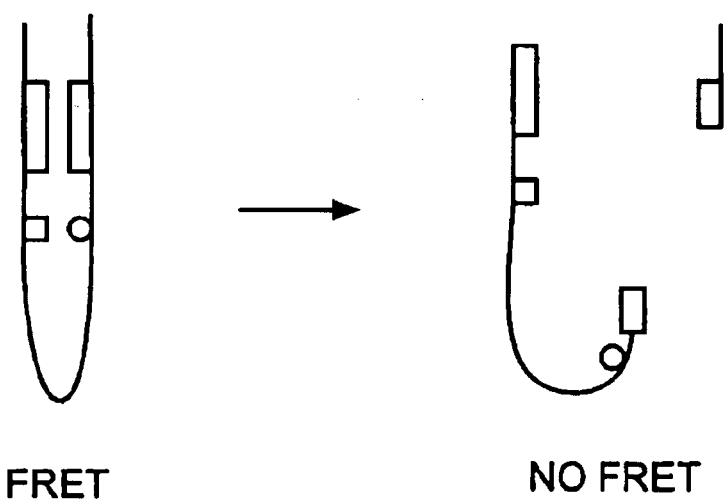
FIG. 5 is a diagrammatic representation of a single-polypeptide reagent useful according to the invention.

In a second example one or more of the labels may not be cleaved from the molecule by the protease, but rely on distancing of the labels to lead to loss of FRET (FIG. 5).

Configuration Using Multiple Fluorescent Emissions

Interaction or association of polypeptides may be measured by any suitable means as set out in this application. It will be recognised by those skilled in the art that some means of detection allow the monitoring of multiple pairs of interacting polypeptides by choosing the fluorophore labels in such a way that different pairs of polypeptides are labelled with different colour fluors (ie. FRET pairs which are configured such that their absorption and/or emission spectra are different from one another).

By practising the invention in this manner, it will be possible to measure association of a first pair of polypeptides by exciting with a first excitation wavelength and monitoring a first emission wavelengh, and to measure association of a second pair of polypeptides by exciting with a second excitation wavelength and monitoring a second emission wavelengh, both the first and second polypeptide pairs being present in the same sample.

Clearly, two such pairs may have similar absorption wavelengths, with different emission wavelengths, or may have different absorption wavelengths with similar emission wavelengths, or may differ from one another in both their absorption and emission wavelengths. It will be understood that for the practice of the invention in this manner, the only requirement is that the fluors are arranged in such a way that FRET pairs may be separately monitored or otherwise distinguished.

The only limitation to the number of polypeptide pairs which may be monitored in solution in the same sample is the number of different combinations of suitable fluorophores which are available.

Fluorophores or FRET pairs with different absorption/emission wavelengths are well known to those skilled in the art, and some examples of these are presented in Table 1.

General Techniques Useful in the Invention

In the present invention, use is made of general techniques of biochemistry and molecular biology as described, for example, in Sambrook et al. as referred to above. Generally, such techniques are useful in the design of polypeptide molecules, and multimers thereof, according to the invention; the production thereof, especially by recombinant DNA techniques; the attachment of labels to the molecules; in the incubation of molecules according to the invention with protease enzymes; and the design of assay protocols to monitor protease activity.

Design of Polypeptides

This is described in the foregoing sections on polypeptide design.

Production of Molecules

Molecules according to the invention are advantageously produced in insect cell systems. Insect cells suitable for use in the method of the invention include, in principle, any lepidopteran cell which is capable of being transformed with an expression vector and expressing heterologous proteins encoded thereby. In particular, use of the Sf cell lines, such as the *Spodoptera frugiperda* cell line IPBL-SF-21 AE (Vaughn et al., (1977) In Vitro, 13, 213–217) is preferred. The derivative cell line Sf9 is particularly preferred. However, other cell lines, such as Tricoplusia ni 368 (Kurstack and Marmorosch, (1976) Invertebrate Tissue Culture Applications in Medicine, Biology and Agriculture. Academic Press, New York, USA) may be employed. These cell lines, as well as other insect cell lines suitable for use in the invention, are commercially available (e.g. from Stratagene, La Jolla, Calif., USA).

As well as expression in insect cells in culture, the invention also comprises the expression of polypeptides in whole insect organisms. The use of virus vectors such as baculovirus allows infection of entire insects, which are in some ways easier to grow than cultured cells as they have fewer requirements for special growth conditions. Large insects, such as silk moths, provide a high yield of heterologous protein. The protein can be extracted from the insects according to conventional extraction techniques.

Expression vectors suitable for use in the invention include all vectors which are capable of expressing foreign proteins in insect cell lines. In general, vectors which are useful in mammalian and other eukaryotic cells are also applicable to insect cell culture. Baculovirus vectors, specifically intended for insect cell culture, are especially preferred and are widely obtainable commercially (e.g. from Invitrogen and Clontech). Other virus vectors capable of infecting insect cells are known, such as Sindbis virus (Hahn et al., (1992) PNAS (USA) 89, 2679–2683). The baculovirus vector of choice (reviewed by Miller (1988) Ann. Rev. Microbiol. 42, 177–199) is *Autographa* californica multiple nuclear polyhedrosis virus, AcMNPV.

Typically, the heterologous gene replaces at least in part the polyhedrin gene of AcMNPV, since polyhedrin is not required for virus production. In order to insert the heterologous gene, a transfer vector is advantageously used. Transfer vectors are prepared in *E. coli* hosts and the DNA insert is then transferred to AcMNPV by a process of homologous recombination.

Alternatively, molecules according to the invention may be expressed in bacterial, lower eukaryote or mammalian cell systems, or in transgenic animals.

cDNA or genomic DNA encoding polypeptides according to the invention can be incorporated into vectors for expression. As used herein, vector (or plasmid) refers to discrete elements that are used to introduce heterologous DNA into cells for either expression or replication thereof. Selection and use of such vehicles is well within the skill of the artisan. Many vectors are available, and selection of the appropriate vector will depend on the intended use of the vector, the size of the DNA to be inserted into the vector, and the host cell to be transformed with the vector. Each vector contains various components depending on its function and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain nucleic acid sequences that enable the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2 m plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in *E. coli* and then the same vector is transfected into yeast or mammalian cells even though it is not capable of replicating independently of the host cell chromosome. DNA may also be replicated by insertion into the host genome. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript© (vector or a pUC plasmid, e.g. pUC18 or pUC19, which contain both *E. coli* replication origin and *E. coli* genetic marker conferring resistance to antibiotics, such as ampicillin.

Suitable selectable markers for mammalian cells are those that enable the identification of cells which have taken up vectors according to the invention, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes a polypeptide according to the invention. Amplification is the process by which genes in greater demand for the production of a protein critical for growth, together with closely associated genes which may encode a desired protein, are reiterated in tandem within the chromosomes of recombinant cells. Increased quantities of desired polypeptide are usually synthesised from thus amplified DNA.

Expression and cloning vectors usually contain a promoter that is recognised by the host organism and is operably linked to a coding sequence. Such a promoter may be inducible or constitutive. The promoters are operably linked to DNA encoding a polypeptide according to the invention by removing the promoter from the source DNA by restriction enzyme digestion and inserting the isolated promoter sequence into the vector. Both the native promoter sequence associated with the polypeptide in question, where this is naturally occurring, and many heterologous promoters may be used to direct amplification and/or expression of nucleic acids. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Their nucleotide sequences have been published, thereby enabling the skilled worker to operably ligate them to DNA encoding a polypeptide according to the invention, using linkers or adaptors to supply any required restriction sites. Promoters for use in bacterial systems will also generally contain a Shine-Delgarno sequence operably linked to the DNA encoding a polypeptide according to the invention.

Preferred expression vectors are bacterial expression vectors which comprise a promoter of a bacteriophage such as phagex or T7 which is capable of functioning in the bacteria. In one of the most widely used expression systems, the nucleic acid encoding the fusion protein may be transcribed from the vector by T7 RNA polymerase (Studier et al, Methods in Enzymol. 185; 60–89, 1990). In the *E. coli* BL21(DE3) host strain used in conjunction with pET vectors, the T7 RNA polymerase is produced from the λ-lysogen DE3 in the host bacterium and its expression is under the control of the IPTG inducible lac UV5 promoter. This system has been employed successfully for overproduction of many proteins, Alternatively the polymerase gene may be introduced on a lambda phage by infection with an int-phage such as the CE6 phage which is commercially available (Novagen, Madison, USA). Other vectors include vectors containing the lambda PL promoter such as PLEX (Invitrogen, NL), vectors containing the trc promoters such as pTrcHisXpress™ (Invitrogen) or pTrc99 (Pharmacia Biotech, SE), or vectors containing the tac promoter such as pKK223-3 (Pharmacia Biotech) or PMAL (new England Biolabs, MA, USA).

Moreover, the nucleic acids encoding polypeptides according to the invention preferably include a secretion sequence in order to facilitate secretion of the polypeptide from bacterial hosts, such that it will be produced as a soluble native peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI or ADHII gene, the acid phosphatase (PHO5) gene, a promoter of the yeast mating pheromone genes coding for the a- or a-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, the *S. cerevisiae* GAL 4 gene, the *S. pombe* nmt 1 gene or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PHO5 promoter is e.g. a shortened acid phosphatase PH05 promoter devoid of the upstream regulatory elements (UAS) such as the PH05 (−173) promoter element starting at nucleotide-173 and ending at nucleotide-9 of the PH05 gene.

Gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus, and Simian Virus 40 (SV40), from heterologous mammalian promoters such as the actin promoter or a very strong promoter, e.g. a ribosomal protein promoter, and from the promoter normally associated with the naturally occurring sequence encoding the polypeptide at issue, provided such promoters are compatible with the host cell systems.

Transcription of a DNA encoding a polypeptide according to the invention by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the vector at a position 5' or 3' to the coding sequence, but is preferably located at a site 5' from the promoter.

Advantageously, a eukaryotic expression vector encoding a polypeptide according to the invention may comprise a locus control region (LCR). LCRs are capable of directing high-level integration site independent expression of transgenes integrated into host cell chromatin, which is of importance especially where the gene is to be expressed in the context of a permanently-transfected eukaryotic cell lint in which chromosomal integration of the vector has occurred, in vectors designed for gene therapy applications or in transgenic animals.

Eukaryotic expression vectors will also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding the polypeptide according to the invention.

An expression vector includes any vector capable of expressing nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding a polypeptide according to the invention may be inserted into a vector suitable for expression of cDNAs in mammalian cells, e.g. a CMV enhancer-based vector such as pEVRF (Matthias, et al., (1989) NAR 17, 6418).

Particularly useful for practising the present invention are expression vectors that provide for the transient expression of DNA encoding polypeptides according to the invention in mammalian cells. Transient expression usually involves the use of an expression vector that is able to replicate efficiently in a host cell, such that the host cell accumulates many copies of the expression vector, and, in turn, synthesises high levels of polypeptides according to the invention. For the purposes of the present invention, transient expression systems are useful e.g. for identifying mutants of polypeptides according to the invention, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

In accordance with another embodiment of the present invention, there are provided cells containing the above-described nucleic acids. Such host cells such as prokaryote, yeast and higher eukaryote cells may be used for replicating DNA and producing polypeptides according to the invention. Suitable prokaryotes include *eubacteria*, such as Gram-negative or Gram-positive organisms, such as *E. coli*, e.g. *E. coli* K-12 strains, DH5α (and HB101, or Bacilli. Further hosts suitable for polypeptides according to the invention encoding vectors include eukaryotic microbes such as filamentous fungi or yeast, e.g. *Saccharomyces cerevisiae*. Higher eukaryotic cells include insect and vertebrate cells, particularly mammalian cells, including human cells, or nucleated cells from other multicellular organisms. In recent years propagation of vertebrate cells in culture (tissue culture) has become a routine procedure. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of nucleic acid encoding polypeptides according to the invention. The precise amounts of such nucleic acid may be empirically determined and optimised for a particular cell and assay.

Host cells are transfected or, preferably, transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby polypeptides according to the invention encoded by the DNA is expressed. The composition of suitable media is known to those in the art, so that they can be readily prepared. Suitable culturing media are also commercially available.

Labelling of Polypeptides

Many amino acid residues have chemistry allowing labelling with commercially available fluorescent and other labels. The most significant of these are those with ionizable side chains—aspartic acid, glutamic acid, lysine, arginine, cysteine, histidine and tyrosine. The labelling reagent will comprise a group conferring the desired property such as fluorescence and a group involved in the conjugation of label to target. The most commonly used functional groups in this context are those which react with amines by either an acylation or alkylation route. These include isothiocyanates, isocyanates, acyl azides, NHS esters and many others. Also common is the use of thiol-directed groups such as haloacetates and maleimides. These label primarily at the free sulfhydryl group of a cysteine residue.

A number of protocols have been devised to achieve labelling at a specific site in a synthesised peptide. These are available in the literature and many are detailed in *Bioconjugate Techniques*, G. T. Hermanson, Academic Press 1996. It is important to note that, while it is possible to bias reactions to achieve specific labelling on one functional group and to prevent promiscuous reaction of the label with other sites in the peptide or protein, it is unlikely to be possible to label, for example, one lysine specifically in a peptide containing multiple amine groups. To achieve this, labelling of the molecule is preferably concurrent with synthesis. This may be achieved either by the use of a labelled amino acid in the synthesis process or by the specific deprotection and labelling of the residue of interest before deprotection of other potentially reactive residues at the completion of the synthesis.

Incubation of Polypeptides in Assays According to the Invention

Buffer/ionic strength—the incubation solution should comprise an appropriate buffer (as defined above) and should be of an ionic strength suitable for the formation of a folded reporter molecule structure (0–150 mM of a suitable salt).

Concentration—peptides should be present at a concentration sufficiently high to allow formation of the folded reporter molecule and detection of the assay output (within the limits of instrumentation) but not so high that the detector is saturated.

Temperature—the temperature selected will be suitable for both formation of the reporter multimer and also activity of any biological agents included in the assay (i.e. 4–40° C.).

Note that each of these parameters are preferably empirically determined as the behaviour of the reporter molecule will be sequence dependent.

The invention is described below, for the purpose of illustration only, in the following examples. Modifications of the techniques described herein will be apparent to those skilled in the art.

General Methods Useful for the Detection of Proteolysis
Purification of proteolytic enzymes
Synthesis of coiled coil peptides
Labelling coiled coil peptides with fluorophores
Purification of fluorescent peptides
Proteolysis of peptides in vitro
Fluorescence measurement of proteolysis in vitro in real time
Reporter group proteolysis in living cells
Heterologous expression of peptides.
Purification of Proteolytic Enzymes The proteases described can be purified from natural sources or from cells/organisms engineered to heterologously express the enzymes. All enzymes used to illustrate the current invention are available commercially. Details of the purifications from natural sources are shown in table 3. Purification from a recombinant source can be achieved by one of several standard methods including the use of a histidine tag as an extension to the protein for purification on a nickel chelating affinity column (used for purification of TEV protease).

TABLE 3

| Protease | Source | Reference |
|---|---|---|
| Chymotrypsin | bovine pancreas | |
| Thrombin | bovine plasma | |
| TEV | recombinant, E. coli (histidine tag) | Life Technologies Ltd. |
| Aminopeptidase M | porcine kidney | |
| Carboxypeptidase P | Penicillium janthinellum | |
| Carboxypeptidase Y | yeast | Hayashi, R., Moore, S. & Stein, W. H., Journal of Biological Chemistry (1973) 248 2296–2302 |

Synthesis of Coiled Coil Peptides

Coiled coil peptides are synthesised by Fmoc or Tboc chemistry according to the methods of Atherton, E., Logan, C. J., & Sheppard (1981), J. Chem. Soc. 1981 538–546 and Perkin, I. & Merrifield R. B. (1963) J. Am. Chem. Soc. 85, 2149–2154 respectively. Following deprotection and cleavage from the resin, peptides are desalted by gel filtration chromatography and analysed by mass spec, HPLC and Edman degradation sequencing using standard methodologies.

Labelling Coiled Coil Peptides With Fluorophores

Coiled coil peptides are labelled with thiol reactive or primary amine reactive derivatives of fluorescein and tetramethylrhodamine or other suitable FRET partners (see table 4; Molecular Probes, Eugene, Oreg., USA) using procedures described by Hermanson, G. T. (1995) Bioconjugate Techniques, Academic Press, London.

TABLE 4

| Donor | Acceptor | $R_0$ (Å) |
|---|---|---|
| Fluorescein | Tetramethylrhodamine | 55 |
| IEDANS (5-((((2-iodoacetyl)-amino)ethyl)amino)-naphthalene-1-sulfonic acid) | Fluorescein | 46 |
| EDANS (5-((2-aminoethyl)-amino)naphthalene-1-sulfonic acid) | DABCYL (4-((4-(dimethylamino)phenyl) azo)benzoic acid) | 33 |
| Fluorescein | Fluorescein | 44 |
| BODIPY ™ FL (4,4-difluoro-5,7-dimethyl-4-bora-3a,4a-diaza-s-indacene-3-propionic acid) | BODIPY ™ FL | 57 |

Purification of Fluorescent Peptides

Fluorescent peptides are separated from unreacted fluorophores by gel filtration chromatography or reverse phase HPLC.

Proteolytic Cleavage of Peptides

Chymotrypsin—Lyophilised chymotrypsin is dissolved in 1 mM HCl. Peptides (0.001–100 µM) are cleaved by chymotrypsin (1:200–1:20 w/w) in either 100 mM Tris-HCl pH 7.5, 12 mM NaCl, 10 mM $CaCl_2$ or 50 mM HEPES pH 7.0, 120M NaCl, 10 mM $CaCl_2$, at 1–40° C. for periods of time ranging from 0 to 24 hours.

Thrombin—Peptides (0.001–100 µM) are cleaved by thrombin (1:100–1:10 w/w) in either 50 mM Tris-HCl, pH 8.0, 120 mM NaCl, 2.5 mM $CaCl_2$, (0.1% 2-mercaptoethanol if required); or 50 mM HEPES pH 7.0, 120 mM NaCl, 2.5 mM $CaCl_2$ at 1–40° C. for periods of time ranging from 0 to 24 hours.

Aminopeptidase M—Peptides (0.001–100 µM) are cleaved by Aminopeptidase M (1:50–1:500 w/w) in 42.2 mM $K_2HPO_4$, 7.8 mM $KH_2PO_4$, pH 7.0, 120 mM NaCl, at 1–40° C. for periods of time ranging from 0 to 24 hours.

Carboxypeptidase Y—Peptides (0.001–100 µM) are cleaved by Carboxypeptidase Y (1:200–1:20 w/w) in 50 mM sodium citrate pH 6.0, 120 mM NaCl, or 42.2 mM $K_2HPO_4$, 7.8 mM $KH_2PO_4$, pH 7.0, 120 mM NaCl at 1–40° C. for periods of time ranging from 0 to 24 hours.

Carboxypeptidase P—Peptides (0.001–100 µM) are cleaved by Carboxypeptidase P (1:100–1:10) in 50 mM sodium citrate pH 4.0, 120 mM NaCl; or 42.2 mM $K_2HPO_4$, 7.8 mM $KH_2PO_4$, pH 7.0, 120 mM NaCl at 1–40° C. for periods of time ranging from 0 to 24 hours.

TEV-Peptides (0.001–100 µM) are cleaved by TEV (1:300–1:30 w/w) in 50 mM Tris-HCl (pH 7), 0.5 mM EDTA, 1 mM DTT, 120 mM NaCl; or 42.2 mM $K_2HPO_4$, pH 7.0, 7.8 mM $KH_2PO_4$, 0.5 mM EDTA pH 7.0 at 1–40° C. for periods of time ranging from 0 to 24 hours.

In each case reactions are monitored in a 1 cm cell in a JASCO 715 spectropolarimeter, the CD at 222 m was observed to follow any change in structure of the peptides present (Circular Dichroism and Optical rotary Dispersion of proteins and polypeptides, Alder, A. J., Greenfield, N. J. & Fasman G. D., Methods in Enzymology (1973) 27 675–796). To confirm the time course of the reaction samples were quenched in 1 mM PMSF or by other suitable means and analysed by mass spectrometry using standard methods.

Fluorescence Measurements of Proteolysis in Vitro in Real Time

Fluorophore labelled coiled coil peptide's (in a 1:6 molar ratio of fluorescein-labelled (pepF) to tetramethylrhodamine-labelled (pepR) peptide) are mixed. Samples are analysed in a fluorimeter using excitation wavelengtbs relevant to pepF (~450 nm) and emission wavelengths relevant to pepF (~516 nm) and pepR (~580 nm). A ratio of emission from pepR over that from pepF following excitation at a single wavelength is used to determine the efficiency of FRET between fluorophores, and hence their spatial proximity. Typically the measurements are performed at 0–37° C. as a function of time following the addition of the relevant protease in an appropriate buffer as detailed above.

Reporter Group Proteolysis in Living Cells

PepF:PepR (where pepF and pepR represent reporter sequences specific for caspase activity) are microinjected into live cells (e.g. Jurkat or HeLa cells). The ratio of emission from pepR/pepF is measured as described above via a photomultiplier tube focused on a single cell. Induction of apoptosis is achieved by treating with anti-Fas monoclonal antibody or TNF-α plus cycloheximide respectively as described in Cryns et al., J. Biol. Chem (1996) 271 31277–31282. Caspase activity is monitored as a change in the ratio of pepR/pepF fluorescence.

Heterologous Expression of Peptides

Coiled coil peptides can be synthesised from the heterologous expression of cDNA sequences for coiled coil domains of interest modified to include the sequence for proteolytic modification as appropriate, or synthetic gene of the same. Expression can be in prokaryotic or eukaryotic cells using a variety of plasmid vectors capable of instructing heterologous expression. Purification of these products is achieved by destruction of the cells (e.g. French Press) and chromatographic purification of the products. This latter procedure can be simplified by the inclusion of an affinity purification tag at one extreme of the peptide, separated from the peptide by a protease cleavage site (other than that of interest) if necessary.

Heterologous expression of the peptides as described above can also be adapted to facilitate in vitro or in vivo assay of proteolytic events. The cDNA or synthetic gene used would code for the peptide to be expressed fused to a variant of GFP, at the N or C terminus. Two plasmids or a plasmid carrying two genes would be introduced such that two peptides are expressed, capable of forming a dimer and fused with different GFP variants capable of FRET. Thus, on expression of the two peptides, a dimer would form and FRET would be observed. Cleavage events would destroy the dimer and FRET would be lost. The expression of the peptides in the cell to be investigated removes the need for microinjection of the reporter peptides.

EXAMPLE 1

Chymotrypsin Assay

Chymotrypsin is a digestive enzyme found in the small intestine. The coiled coil peptide of GCN4 can be adapted to provide a homodimeric reporter molecule able to monitor cleavage by chymotrypsin in the manner described above.

The position of the labelling site is determined as follows—

The label must be in a position where:
it does not interfere substantially with the assembly of the reporter molecule at the reaction temperature (in the coiled coil, modifications to positions b, c or f are least disruptive; positions e and g are more disruptive; and positions a and d are most disruptive to coil formation)

it is sufficiently far from the site of chemical modification not to interfere with enzyme activity it is in a highly structured region of the reporter to ensure that the position and orientation of the labels with each other can be well understood (in a coiled coil this preferably entails avoiding a position in the terminal heptads)

the labels are as close in space as is possible given other constraints.

An assessment of potential locations is made using any structural information available and also homology with other known structures.

Peptide A is synthesised, incorporating a C residue at position 273 for labelling purposes:

RMKQLEDKVEELLSKTY-HLENEVACLKKLVGERAAK    Peptide A
(SEQ ID NO:24)

This sequence is derived from that of amino acids 249–281 of GCN4 (Genbank Accession No. K02205.

(X-X represents the protease cut site, Y residue in bold indicates the recognition feature of the enzyme).

$N_{264}$ has been changed to T, and $R_{273}$ has been changed to C. The tyrosine residue (shown here in bold type) is the residue at which chymotrypsin cleaves. The cysteine residue (also shown in bold type) provides the site for attachment of thiol-directed fluorescent labels.

The circular dichroism (measured in units of ellipticity) of proteins at 222 nm provides a measure of the amount of α-helix present in the structure, with a large, negative ellipticity indicting a high level of helicity. The coiled-coil has a distinctive α-helical CD spectrum with minima at 222 nm and 208 nm (O'Shea et al., 1989, *Science*, 243: 538–542). A timecourse of peptide A cleavage by chymotrypsin (20:1 w/w) is followed by digesting 10 μM peptide A in 50 mM Tris-HCl pH 7.5, 50 mM NaCl, 10 mM $CaCl_2$ at 30° C. in a JASCO 715 spectropolarimeter and observing the change in θ at 222 nm. A wavelength scan (260–200 nm) is also taken of the sample at the start and end of the experiment. These data show that peptide cleavage by chymotrypsin results in the loss of coiled coil structure as required by the assay, supporting the fluorimetric data presented below.

A time-course digestion of Peptide A with chymotrypsin is analysed by MALDI-TOF mass spectrometry. On the protein matrix (MS, denoted SA on each spectrogram) the Peptide A substrate as 4245Da is evident. It is degraded completely over two hours to a fragment of 2155 Da (which is the N-terminal fragment, cleaved at the Y—H bond). The C-terminal fragment appears to be cleaved at a second site (after L-26) generating a product of 1100 Da, although the final peptide fragment of about 990 Da is not observed in the MS.

Peptides are then labelled using a method adapted from one known in the art (Hermanson, 1997, *Bioconjugate Techniques*, Academic Press). 20 mM fluorescein iodoacetamide (IAF), or 20 mM tetramethylrhodamine iodoacetamide (TMRIA) in DMSO and 0.23 mM peptide in 20 mM TES buffer, pH 7.0 are prepared. Fluorophore and peptide are mixed in a molar ratio of 0.9:1 (label:peptide) and incubated at 4° C. in the dark for a minimum of 2 hours. Labelling is assessed by reverse phase HPLC (C18 column; solvent A: $H_2O$/0.1% TFA; solvent B: acetonitrile/0.1% TFA) and MALDI-TOF mass spectrometry. Peptide A labelled with fluorescein (Peptide AF) and rhodamine (Peptide AR) are thus generated.

FRET occurs between fluorophores attached to undigested peptides, which interact with each other, but not between digested peptides, which do not interact (evidenced by loss of structure in CD experiments). Only the fluorescence emission quench of the donor fluorophore is displayed in these experiments.

Fluorescence at 516 nm is measured for labelled peptide A in a 1 cm pathlength cell at peptide concentrations of 0.08 µM peptide AF and 0.48 µM peptide AR in 50 mM HEPES pH 7.0, 150 mM NaCl, 10 nM CaCl$_2$ at 30° C. in a PTI fluorimeter system with temperature controlled by a waterbath. Upon addition of peptide AR to peptide AF, fluorescence in the region of fluorescein emission decreases. This suggests that energy transfer is taking place.

A timecourse of peptide A cleavage by chymotrypsin is followed by digesting 8 µM AF and 48 µM AR in 50 mM HEPES pH 7.0, 150 mM NaCl, 10 mM CaCl$_2$ at ~30° C. Samples are removed at 10 minute intervals and diluted 100×into 50 mM HEPES pH 7.0, 150 mM NaCl, 10 mM CaCl$_2$, and an emission scan (excitation wavelength 450 nm) is recorded at ~30° C. for each diluted sample. This data is presented as a ratio of emission 580 nm/emission 515 nm to eliminate any concentration differences introduced on dilution of the samples. A decrease in this ratio represents loss of FRET which is correlated with peptide cleavage. The fluorometric data gathered over this timecourse corresponds well with that observed by MALDI-TOF, a plateau being reached by 2 hours which is the time point at which the mass spectrometric data.

In addition, no FRET is observed when the cleaved fluorescein labelled peptide A (peptide ADF) is mixed with peptide AR, indicating that when even one polypeptide partner is digested, formation of the coiled coil structure and, hence, protein:protein heterodimerisation (with respect to fluorophore composition) cannot occur.

Together, these results, that FRET does not occur between the digested molecules or between a digested and an undigested molecule, indicated that FRET using labelled, polypeptides comprising a coiled-coil, may be used successfully in the invention to report on the digestion of polypeptides by proteolytic enzymes.

EXAMPLE 2

Amino- and Carboxypeptidases

Exopeptidases are important in the breakdown of peptides after initial digestion by endopeptidases such as chymotrypsin or trypsin. The end product of attack by such enzymes are free amino acids or dipeptides. An assay for this type of proteolysis relies upon the fluorophores being far from the initial site of proteolysis such that digestion ultimately results in a fragment which is too small to remain within the coiled coil multimer, at which point FRET is lost. An unblocked N-terminus or C-terminus is essential for the activity of exopeptidases.

Artificial designer peptides are synthesised such that a heterodimeric coiled coil is formed upon mixing of the partners.

| | |
|---|---|
| IAALRERICYLRERNQQLRQRIQQL (SEQ ID NO:25) | peptide B |
| acetyl-IAALEREIYKLEQENQQLEQEIQQL-amide (SEQ ID NO:26) | peptide C |

Peptides B and C are labelled as set forth in example 1, to produce BF and CR (or vice versa), labelled with fluorescein and rhodamine respectively.

Upon mixing, FRET is observed as heterodimers are formed. When peptides BF and CR are incubated in the presence of aminopeptidase M or carboxypeptidase Y, together with an appropriate buffer, FRET is lost due to digestion of the coiled coil to a point where structure can no longer be maintained.

EXAMPLE 3

TEV (Tobacco Etch Virus) Protease

This protease is important in the processing of the precursor polyprotein of TEV (Mutational analysis of Tobacco Etch Virus polyprotein processing: cis and trans proteolytic activities of polyproteins containing the 49-kilodalton proteinase, Carrington, J. C., Cary, S. M. & Dougherty, W. G., Journal of Virology (1988) 62 2313–2320). In the laboratory it is commonly used in the cleavage of affinity tags from recombinant proteins after the purification process (Release of proteins and peptides from fusion proteins using a recombinant plant virus proteinase, Parks, T. D., Leuther, K. K., Howard, E. D., Johnston, S. A. & Dougherty, W. G., Analytical Biochemistry (1994) 216 413–417). The seven amino acid recognition site allows highly specific cleavage and makes undesirable cleavage of the recombinant protein unlikely.

| | |
|---|---|
| RMKQLEDKVENLYSQ-SYHLENEVACLKKLVGER (SEQ ID NO:27) | Peptide 2 |

Peptide 2 is constructed to contain the TEV protease cleavage site, and labelled at an inserted unique cysteine residue, as for Peptide A. The labelling and FRET assay of Example 1 is repeated, with identical results.

EXAMPLE 4

Thrombin

Thrombin is the final enzyme in the blood clotting cascade, cleaving fibrinogen to fibrin. Its effects are, in part, regulated by a negative feedback mechanism in which thrombin activates protein C which ultimately switches off the cascade and therefore thrombin production. This enzyme is also important in promoting mitosis in fibroblasts, chemotaxis in monocytes and neurite retraction in neurons. The coiled coil peptide of GCN4 can be adapted to provide a homodimeric reporter molecule to monitor cleavage by thrombin in the manner described above. In order to have cleavage at one site only it is necessary to eliminate all arginine residues other than that at the intended cleavage site from the peptide (as in Peptide 3 below).

| | |
|---|---|
| KMKQLEDKVR-ELLSKNYHLENEVACLLKKLVGER (SEQ ID NO:28) | Peptide 3 |

The procedure of Example 1 is repeated with Peptide 3, and again identical results are obtained.

EXAMPLE 5

Caspases

The caspases (Caspases: enemies within, Thornberry, N. A. & Lazebnik, Y. (1998) Science 281 1312–1316) are a family of proteases with an absolute requirement for cleavage after aspartic acid. They are synthesised as inactive proenzymes and cleaved either autocatalytically or by another member of the family to form an active heterodimer of a large and a small subunit. This family of enzymes play a role in inflammation but, more importantly, several members of the family provide signals triggering apoptosis of the cell and others are directly involved in cell disassembly itself. The role of caspases in the apoptotic process includes the inactivation of proteins protective against apoptosis such as the Bcl-2 proteins, the destruction of proteins with a key role in cell structure such as the lamins and the deregulation of proteins by the disruption of links between regulatory and effector domains. A loss of control of apoptosis leading either to excessive or inadequate cell death plays a role in many disease processes including cancers, neurodegenerative disorders and auto-immune disease. Evidence is already available suggesting that caspase inhibitors are able to protect against inappropriate cell death.

The coiled coil peptide of GCN4 is adapted to provide a homodimeric reporter molecule to monitor cleavage by members of the caspase family (e.g. for Caspase 2, 3, 7 below) in the manner described above.

| | |
|---|---|
| RMKQLEDKVEELLDEND-HLENEVACLKKLVGER (SEQ ID NO:29) | Peptide 4 |

The procedure of Example 1 is repeated with Peptide 4, and identical results are obtained.

EXAMPLE 6
Fatty Acylation and GPI Anchor Attachment

As discussed above, the assay format according to the invention can be extended to measure post-translational modification events which have proteolysis as an integral step. The molecular basis of these assays is the destabilisation of the binding partnership following the proteolytic event which, if coincident with the covalent addition of another group (GPI, farnesyl etc.), provides an indirect reporter function for these classes of post-translational modification.

Fatty acylation of proteins is a dynamic post-translational modification which is critical for the biological activity of many proteins, as well as their interactions with other proteins and with membranes. Thus, for a large number of proteins, the location of the protein within a cell can be controlled by its state of prenylation (fatty acid modification) as can its ability to interact with effector enzymes (ras and MAP kinase, Itoh, T., Kaibuchi, T., Masuda, T., Yamamoto, T., Matsuura, Y., Maeda, A., Shimizu, K., & Takai, Y. (1993) J. Biol. Chem. 268, 3025-; ras and adenylate cyclase (in yeast) Horiuchi, H., Kaibuchi, K., Kawamura, M., Matsuura, Y., Suzuki, N., Kuroda, Y., Kataoka, T., & Takai, Y. (1992) Mol. Cell. Biol. 12, 4515-) or with regulatory proteins (Shirataki et al., 1991, above). The prenylation status of ras is important for its oncogenic properties (Cox, 1995, above) thus interference with the prenylation status of ras is considered a valuable anti-cancer strategy (Hancock, J. F. (1993) Current Biology 3, 770)

The coiled coil of GCN4 is adapted to produce a homodimeric reporter molecule capable of monitoring geranylgeranylation according to the procedure described in Example 1. The adaptations are (i) to shorten the length of the coiled-coil structure to achieve a coiled coil oligomer of reasonable stability; (ii) to modify the C-terminal residues as necessary to comply with the substrate recognition features of geranylgeranyltransferase I (GGT I).

| | |
|---|---|
| KVEELLSKNYHLENEVARLKCALL (SEQ ID NO:30) | Peptide 5 |

The recognition site is detailed in bold, the underlined cysteine is the site of geranylgeranylation. The concomitant proteolytic removal of the C-terminal residues (ALL) will result in destabilisation of the coiled-coil structure and will prompt dissociation of the oligomer. This can be used as an indirect measure of fatty acylation. A change in the C-terminal amino acid (to Ser, Met, Ala or Gln) alters the specificity of this reporter to measure farnesylation (Protein prenyltransferases, Casey, P. J & Seabra, M. C., Journal of Biological Chemistry (1996) 271 5289–5292).

Labelling for FRET is achieved in two ways: by N-terminal capping and mutation of the existing K to R, thus providing a primary amine to which a fluorophore may be attached, or by incorporation of fluorescent residues during peptide synthesis (see above).

Peptide 5 is labelled with fluorescein or rhodamine, and assayed for FRET under the conditions of Example 1. Geranylgeranylation is then performed by incubating 1–4 µg of the reporter molecule with 25 µl rabbit reticulocyte lysate (or the equivalent quantity of either a purified geranylgeranyltranferase or a test sample) and geranylgeranyl pyrophosphate (40 µM) in a final volume of at least 50 µl (Cox 1995, above). The modification of the reporter is followed by observation of acceptor/donor fluorescence emission upon excitation of the donor fluorophore at an appropriate wavelength. A decrease in this ratio indicates a loss of FRET which is a measure of the geranylgeranylation of the reporter.

A number of membrane proteins are anchored in the membrane through the covalent attachment of a glycosylated phospholipid, most commonly glycosylphosphatidylinositol (GPI), to the C-terminus of the polypeptide (reviewed in Udenfriend, S., & Kodukula, K. (1995) How glycosyl-phosphatidylinositol-anchored membrane proteins are made. Ann. Rev. Biochem. 64, 563–591). These proteins do not have a transmembrane domain made of amino acids, instead covalent attachment of a glycosylated form of phosphatidyl inositol is attached to the C-terminal residue of the protein (reviewed in Udenfriend & Kodukula, 1995; Kinoshita, T., Ohishi, K., & Takeda, J., (1997) GPI-anchor synthesis in mammalian cells: Genes, their products and a deficiency. J. Biochem. (Tokyo) 122, 251–257). This anchors the protein in the (usually plasma) membrane. This form of membrane association permits the release of the polypeptide from the membrane following the hydrolysis of the anchor by the enzyme phospholipase C (or phospholipase D). In the case of plasma membrane associated GPI-anchored proteins this will release the protein from the cell into the blood stream or extracellular solution. Approximately 50 proteins are known to be attached to membranes by this route, including prion proteins, acetylcholinesterase, alkaline phosphatase, folate transporter, urokinase receptor, cell adhesion molecules (N-CAM), trypanosome antigenic proteins (variant surface glycoproteins, malaria), CD-24 (small cell lung carcinoma antigen) (reviewed in Udenfriend & Kodukula, 1995). This can facilitate the shedding of protein antigen (by parasites) to avoid immunodetection.

The attachment of the GPI anchor occurs in the lumen of the ER, and occurs within one minute of protein synthesis in living cells. Proteins targeted for GPI anchoring have at least two primary sequence signals, (i) an N-terminal leader sequence to facilitate their transport into the ER, and (ii) a C-terminal sequence which directs GPI anchor attachment. There is some considerable similarity between these two signals (Yan, W., Shen, F., Dillon, B., & Ratnam, M. (1998) The hydrophobic domains in the carboxyl-terminal signal for GPI modification and in the amino-terminal leader peptide have similar structural requirements. J. Mol. Biol.

275, 25–33.) A schematic representation of the protein structure is as follows:

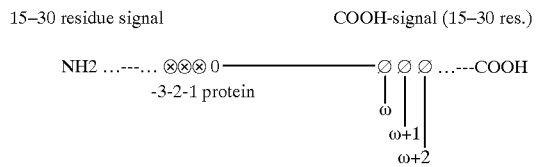

where:
... hydrophilic region (~10 residues in the C-terminal signal)
---hydrophobic region (>12 residues in the C-terminal signal, moderately hydrophobic)
ω is the site of attachment of the GPI anchor.
ω: serine = asparagine>alanine = glycine =aspartate>cysteine>>>valine = leucine
ω+1: glycine, alanine , (serine in trypanosome)>>other amino acids. NOT proline
ω+2: glycine, alanine>serine>theonine>aspartate>valine
Adapted from Udenfriend & Kodukula, 1995.

The aim of this assay is to produce a substrate which oligomerises using a coiled coil interaction, prior to, but not following GPI anchor attachment. The structural feature responsible for oligomerisation must therefore reside within the C-terminal signal sequence for GPI attachment.

Figure 6:
FIG. 6 depicts constructs useful according to the invention.
Figure 6:

A construct is used consisting of the leader sequence and part of the folate receptor (Genbank Accession No: X69516) followed by an artificial sequence containing the consensus sequence for GPI anchor addition which adopts a heteromultimeric coiled-coil (FIG. 6).

In FIG. 6, amino acids in bold represent the GPI anchor attachment site; the underlined sequence is the hydrophilic region and the sequence in italics is the hydrophobic region of the recognition site; X represents the amino acid used for measuring the reporter output, K maybe derivatised with dansyl.

Fluorescently labelled reporter molecules are produced and incorporated in an assay for GPI anchor addition using methods derived from Crowley, K. S., Reinhart, G. D. and Johnson, A. E. (1993) Cell 73, 1101–1115 and Kodukula, K., Micanovic, R., Gerber, L., Tamburrini, M., Brink, L. and Udenfriend, S. (1991) Journal of Biological Chemistry 266, 4464–4470.

Isolation of tRNA$^{lys}$ from 10 mg of unfractionated brewer's yeast tRNA is achieved using fast protein liquid chromatography (FPLC) with a MonoQ HR 10/10 column. Elution was in 10 mM MgCl, 10 mM sodium acetate (pH 4.5) with a linear gradient of NaCl from 0.48M to 11.0M. Fractions enriched in tRNA$^{lys}$ are identified by aminoacylation assays and the nucleic acid precipitated in ethanol. After dialysis the fractions are repurified by FPLC as before and fractions with the highest level of tRNA$^{lys}$ are precipitated, dialysed and aminoacylated with lysine. The aminoacylated tRNA$^{lys}$ is purified by FPLC, precipitated and dialysed into 1 mM potassium acetate (pH5.0) at 4° C. This is stored at −75° C.

tRNA$^{lys}$ prepared as above has been shown to be selectively modified at the ε amino group with NBD using the method of Johnson et al (Johnson, A. E., Woodward, W. R., Herbert, E. and Menninger, J. R. (1976) *N$^ε$-acetllysine transfer ribonucleic acid; a biologically active analogue of aminoacyl transfer ribonucleic acids*. Biochemistry 15, 569–575). We therefore use a parallel method to label tRNA$^{lys}$ with a dansyl group (a good FRET partner for tryptophan). 6-((5-dimethylaminonaphthalene-1-sulfonyl) amino)hexanoic acid, succinimidyl ester (dansyl-X-SE; Molecular Probes) (9 mg) is solubilized in 1.75 ml of dimethylsulphoxide and added to 5 nmol lys-tRNA in 750 ml of 50 mM potassium phosphate (pH7.0). The labelling reaction is initiated by the addition of 15 μl of freshly made 4M KOH while stirring vigorously. The reaction is allowed to proceed for 20 seconds at 20° C. before the addition of 151 of 4M acetic acid to terminate the reaction. The tRNA is immediately ethanol precipitated. Excess free dye is removed by redissolving the pellet and ethanol precipitating the product for a second time. This method yields a high proportion of labelled lys-tRNA which is purified by FPLC using a benzoylated diethylaminoethyl cellulose column. The column is washed with 1M NaCl, 10 mM MgCl$_2$, 10 mM sodium acetate (pH 4.5) and then eluted with 25 ml of 2M NaCl, 10 mM MgCl$_2$, 10 mM sodium acetate (pH4.5), 25% (v/v) ethanol. The dansyl-lys-tRNA is ethanol precipitated, resuspended and dialysed into 1 mM potassium acetate for storage.

Plasmids are prepared carrying the coding sequence for the reporter described above using well known and published methods. The plasmids are linearised and transcribed using a Riboprobe-II kit (Promega Biotech) to generate mRNA for in vitro translation.

Rough microsomal membranes (RM) are prepared from Chinese hamster ovary (CHO) cells. Cells are maintained in Iscove's modified Dulbecco's medium with 10% foetal calf serum (FCS) and are harvested at confluency, washed twice with ice-cold phosphate buffered saline (PBS) and scraped into PBS. These cells are pelleted at 1000×g and washed twice with PBS. Pelleted cells are resuspended in 10 mM Tris (pH7.5) and incubated on ice for 5 minutes. Maintaining a ratio of 1:15 (cells:buffer), the cell suspension is diluted with an equal volume of 600 mM sucrose, 6 mM dithiothreitol and incubated for a further 5 minutes on ice. This suspension is homogenised with 10 strokes in a Dounce homogeniser at 4° C. The homogenate is centrifuged for 2×10 minutes at 7700×g and ×20 minutes at 17,300×g. In each case the pellet is discarded. Centrifugation of the final supernatant at 100,000×g for 60–75 minutes yields rough microsomal membranes.

The fluorescently labelled dansyl-lys-tRNA is used together with an mRNA transcription mix for in vitro translation of the reporter peptides in the presence of rough microsomal membranes using a translation system such as the rabbit reticulocyte lysate supplied by Promega. A 25 μl translation mixture is prepared containing 12.5 μl nuclease-treated rabbit reticulocyte lysate, 0.04 mM mixed amino acids (minus methionine), 12–15 pmol dansyl-lys-tRNA, 20 units RNase inhibitor, 1.5–2.0 μl [$^{35}$S]methionine (15 mCi/ml; 1100 Ci/mmol) and 1–2 μg reporter mRNA. This mixture is preincubated for 2 min at 30° C. before the addition of RM.

RM are resuspended by repetitive pipetting in translation buffer (100 mM KCl, 4 mM Mg$^{2+}$, 50 mM sucrose, 3 mM dithiothreitol and a cocktail of protease inhibitors including aprotinin, antipain, bestatin, chymostatin, leupeptin and pepstatin each at 2 μg/ml and RNase inhibitor at 5 units/ml) and 5 μl of this membrane suspension is added to the translation mixture.

Translations are incubated at 20–30° C. for 25 to 90 minutes. After 5–50 minutes 100-fold excess (1–2 nmol) unlabeled lys-tRNA is added to the translation mixture. This serves to dilute out the labelled dansyl-lys-tRNA, allowing no further fluorescent reporter to be produced. The GPI anchor, in addition to the reporter is observed by exciting the Trp residue in (i) with light of wavelength 280 nm and following acceptor/donor (A/D) emission at appropriate wavelengths (~340 nm and ~520 nm). Initially, FRET will be high, giving a high A/D output. As the processing of the reporter progresses the multimers are forced apart by the addition of the GPI moiety, FRET is lost and the A/D ratio decreases.

EXAMPLE 7
Protection of the Reporter From Promiscuous Modification

In order to configure the assays of Examples 1 to 5 not only to monitor chemical modification in defined systems but also to screen for activities in complex environments (e.g. whole cell lysates) it may be necessary to protect the reporter molecule from proteolysis at sites other than those engineered into the structure. The vast majority of naturally occurring enzymes will not recognise as substrates peptides comprising D amino acids. The specificity of the reporter group will be increased by limiting the use of L amino acids (recognised by enzymes) to residues involved in recognition by the protease. This will greatly reduce the probability of unplanned proteolysis at additional sites by other proteases in, for example, a cell extract.

Figure 7:
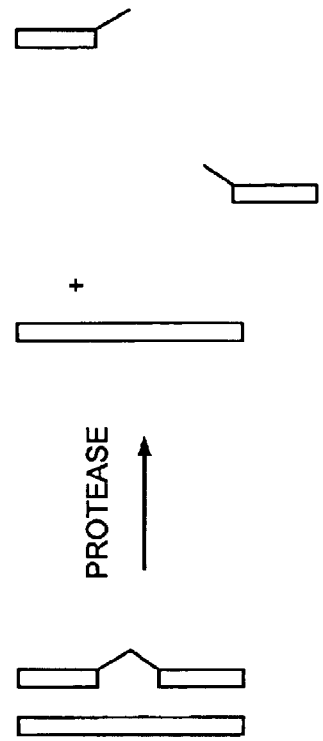
FIG. 7 depicts a reporter molecule useful according to the invention.

Proteins or peptides composed of D amino acids have a structure which is the exact mirror image of that formed with L amino acids (Identification of D-peptide ligands through mirror image phage display, Schumacher, T. N. M., Mayr, L. M., Minor, D. L. Jnr., Milhollen, M. A., Burgess, M. W., Kim, P. S., Science (1996) 271 1854–1857). We therefore conclude that a reporter designed in this way will have a structure of the form shown in the diagram in FIG. 7.

---

What is claimed is:

1. A method of detecting or monitoring the activity of a protease enzyme, comprising the steps of:
   a) providing a first polypeptide binding domain, and a second polypeptide binding domain, wherein
      i) at least one of the binding domains comprises a site for protease digestion and wherein said site for protease digestion is located within said first or second polypeptide binding domain; and
      ii) the first and second binding domains bind to each other such that a detectable signal is generated, and digestion of the binding domains at the site for protease digestion by the protease enzyme results in modulation of the binding of the polypeptides to each other and therefore of the detectable signal;
   b) allowing the binding domains to bind to each other and induce a detectable signal;
   c) contacting the binding domains with a protease enzyme; and
   d) detecting modulation of the detectable signal as a result of the modulation of the binding of the binding domains.

2. A method of detecting or monitoring the activity of a modulator of a protease enzyme, comprising the steps of:
   a) providing a first polypeptide binding domain, and a second polypeptide binding domain, wherein
      i) at least one of the binding domains comprises a site for protease digestion and wherein said site for protease digestion is located within said first or second polypeptide binding domain; and
      ii) the first and second binding domains bind to each other such that a detectable signal is generated, and digestion of the polypeptides at the site for protease digestion by the protease enzyme results in modulation of the binding of the binding domains to each other and therefore of the detectable signal;
   b) allowing the binding domains to bind to each other and induce a detectable signal;
   c) contacting the binding domains with a protease enzyme;
   d) detecting modulation of the detectable signal as a result of the modulation of the binding of the binding domains to determine a reference signal modulation;
   e) contacting the binding domains with a protease enzyme and a candidate modulator of the protease enzyme; and
   f) detecting modulation of the detectable signal as a result of the modulation of the binding of the binding domains to each other, and comparing the modulation detected with the reference signal modulation.

3. The method of claim 1 or claim 2, wherein at least one of the first binding domain or the second binding domain is labeled.

4. The method of claim 3, wherein the label is a fluorescent label.

5. The method of claim 3, wherein the first and second binding domains are associated with a first and second label, respectively.

6. The method of claim 5, wherein the first label on the first binding domain is different from the label on the second binding domain.

7. The method of claim 6, wherein said detectable signal is generated by an interaction between the said first and second labels.

8. The method of claim 6, wherein said interaction comprises energy transfer.

9. The method of claim 1 or claim 2, wherein said detectable signal is generated by a label associated with at least one of said first or second binding domains to diffuse in solution.

10. The method of claim 1 or 2 wherein said digestion comprises cleavage at a protease cleavable site.

11. The method of claim 1 or 2, wherein the binding domains are comprised in separate polypeptides.

12. The method of claim 1 or 2, wherein said first and second binding domains bind to each other to form a multimer; and wherein proteolysis is required for multimer association.

* * * * *

SEQUENCE LISTING

```
<160> NUMBER OF SEQ ID NOS: 32

<210> SEQ ID NO 1
<211> LENGTH: 5
<212> TYPE: PRT
<213> ORGANISM: Rattus norvegicus
<220> FEATURE:
<221> NAME/KEY: BINDING
<222> LOCATION: (1)..(5)
<223> OTHER INFORMATION: Protein binding motif
<220> FEATURE:
<221> NAME/KEY: BINDING
<222> LOCATION: (2)
<223> OTHER INFORMATION: Xaa at position 2 in the protein binding motif
      can be any amino acid

<400> SEQUENCE: 1

Tyr Xaa Asp Glu Asp
 1               5

<210> SEQ ID NO 2
<211> LENGTH: 5
<212> TYPE: PRT
<213> ORGANISM: Rattus norvegicus

<400> SEQUENCE: 2

Glu Asx Ile Ala Pro
 1               5

<210> SEQ ID NO 3
<211> LENGTH: 41
<212> TYPE: PRT
<213> ORGANISM: Homo sapiens

<400> SEQUENCE: 3

Ile Leu Ile Ser Leu Glu Ser Glu Glu Arg Gly Glu Leu Glu Arg Ile
 1               5                  10                  15

Leu Ala Asp Leu Glu Glu Glu Asn Arg Asn Leu Gln Ala Glu Tyr Asp
                20                  25                  30

Arg Leu Lys Gln Gln His Glu His Lys
            35                  40

<210> SEQ ID NO 4
<211> LENGTH: 32
<212> TYPE: PRT
<213> ORGANISM: Saccharomyces cerevisiae

<400> SEQUENCE: 4

Met Lys Gln Leu Glu Asp Lys Val Glu Glu Leu Leu Ser Lys Asn Tyr
 1               5                  10                  15
```

—continued

His Leu Glu Asn Glu Val Ala Arg Leu Lys Lys Leu Val Gly Glu Arg
                20                  25                  30

<210> SEQ ID NO 5
<211> LENGTH: 39
<212> TYPE: PRT
<213> ORGANISM: Homo sapiens

<400> SEQUENCE: 5

Thr Asp Thr Leu Gln Ala Glu Thr Asp Gln Leu Glu Asp Glu Lys Ser
1               5                   10                  15

Ala Leu Gln Thr Glu Ile Ala Asn Leu Leu Lys Glu Lys Glu Lys Leu
                20                  25                  30

Glu Phe Ile Leu Ala Ala His
            35

<210> SEQ ID NO 6
<211> LENGTH: 39
<212> TYPE: PRT
<213> ORGANISM: Homo sapiens

<400> SEQUENCE: 6

Ile Ala Arg Leu Glu Glu Lys Val Lys Thr Leu Lys Ala Gln Asn Ser
1               5                   10                  15

Glu Leu Ala Ser Thr Ala Asn Met Leu Arg Glu Gln Val Ala Gln Leu
                20                  25                  30

Lys Gln Lys Val Met Asn His
            35

<210> SEQ ID NO 7
<211> LENGTH: 38
<212> TYPE: PRT
<213> ORGANISM: Escherichia coli

<400> SEQUENCE: 7

Val Asp Lys Leu Gly Ala Leu Glu Glu Arg Arg Lys Val Leu Gln Val
1               5                   10                  15

Lys Thr Glu Asn Leu Gln Ala Glu Arg Asn Ser Arg Ser Lys Ser Ile
                20                  25                  30

Gly Gln Ala Lys Ala Arg
            35

<210> SEQ ID NO 8
<211> LENGTH: 32
<212> TYPE: PRT
<213> ORGANISM: Escherichia coli

<400> SEQUENCE: 8

Glu Pro Leu Arg Leu Glu Val Asn Lys Leu Gly Glu Glu Leu Asp Ala
1               5                   10                  15

Ala Lys Ala Glu Leu Asp Ala Leu Gln Ala Glu Ile Arg Asp Ile Ala
                20                  25                  30

<210> SEQ ID NO 9
<211> LENGTH: 33
<212> TYPE: PRT
<213> ORGANISM: Thermus thermophilus

<400> SEQUENCE: 9

Asp Leu Glu Ala Leu Leu Ala Leu Asp Arg Glu Val Gln Glu Leu Lys
1               5                   10                  15

```
-continued
```

Lys Arg Leu Gln Glu Val Gln Thr Glu Arg Asn Gln Val Ala Lys Arg
                20                  25                  30
Val

<210> SEQ ID NO 10
<211> LENGTH: 32
<212> TYPE: PRT
<213> ORGANISM: Thermus thermophilus

<400> SEQUENCE: 10

Glu Ala Leu Ile Ala Arg Gly Lys Ala Leu Gly Glu Glu Ala Lys Arg
 1               5                  10                  15

Leu Glu Glu Ala Leu Arg Glu Lys Glu Ala Arg Leu Glu Ala Leu Leu
                20                  25                  30

<210> SEQ ID NO 11
<211> LENGTH: 30
<212> TYPE: PRT
<213> ORGANISM: Escherichia coli

<400> SEQUENCE: 11

Leu Arg Gly Ala Glu Lys Leu Arg Glu Glu Leu Asp Phe Leu Lys Ser
 1               5                  10                  15

Val Phe Arg Pro Glu Ile Ile Ala Ala Ile Ala Glu Ala Arg
                20                  25                  30

<210> SEQ ID NO 12
<211> LENGTH: 26
<212> TYPE: PRT
<213> ORGANISM: Escherichia coli

<400> SEQUENCE: 12

Ala Glu Tyr His Ala Ala Arg Glu Gln Gln Gly Phe Cys Glu Gly Arg
 1               5                  10                  15

Ile Lys Asp Ile Glu Ala Lys Leu Ser Asn
                20                  25

<210> SEQ ID NO 13
<211> LENGTH: 32
<212> TYPE: PRT
<213> ORGANISM: Saccharomyces cerevisiae

<400> SEQUENCE: 13

Met Lys Gln Ile Glu Asp Lys Ile Glu Glu Ile Leu Ser Lys Ile Tyr
 1               5                  10                  15

His Ile Glu Asn Glu Ile Ala Arg Ile Lys Lys Leu Ile Gly Glu Arg
                20                  25                  30

<210> SEQ ID NO 14
<211> LENGTH: 29
<212> TYPE: PRT
<213> ORGANISM: Artificial Sequence
<220> FEATURE:
<223> OTHER INFORMATION: Description of Artificial Sequence: synthetic
      peptide coil

<400> SEQUENCE: 14

Glu Trp Glu Ala Leu Glu Lys Lys Leu Ala Ala Leu Glu Ser Lys Leu
 1               5                  10                  15

Gln Ala Leu Glu Lys Lys Leu Glu Ala Leu Glu His Gly
                20                  25

```
<210> SEQ ID NO 15
<211> LENGTH: 29
<212> TYPE: PRT
<213> ORGANISM: Saccharomyces cerevisiae

<400> SEQUENCE: 15

Glu Trp Glu Ala Leu Glu Lys Lys Leu Ala Ala Leu Glu Ser Lys Leu
 1               5                  10                  15

Gln Ala Leu Glu Lys Lys Leu Glu Ala Leu Glu His Gly
            20                  25

<210> SEQ ID NO 16
<211> LENGTH: 25
<212> TYPE: PRT
<213> ORGANISM: Escherichia coli

<400> SEQUENCE: 16

Gln Glu Lys Thr Ala Leu Asn Met Ala Arg Phe Ile Arg Ser Gln Thr
 1               5                  10                  15

Leu Thr Leu Leu Glu Lys Leu Asn Glu
            20                  25

<210> SEQ ID NO 17
<211> LENGTH: 24
<212> TYPE: PRT
<213> ORGANISM: Escherichia coli

<400> SEQUENCE: 17

Asp Glu Gln Ala Asp Ile Cys Glu Ser Leu His Asp His Ala Asp Glu
 1               5                  10                  15

Leu Tyr Arg Ser Cys Leu Ala Arg
            20

<210> SEQ ID NO 18
<211> LENGTH: 16
<212> TYPE: PRT
<213> ORGANISM: Homo sapiens

<400> SEQUENCE: 18

Leu Ile Leu Ile Cys Leu Leu Leu Ile Cys Ile Ile Val Met Leu Leu
 1               5                  10                  15

<210> SEQ ID NO 19
<211> LENGTH: 5
<212> TYPE: PRT
<213> ORGANISM: Artificial Sequence
<220> FEATURE:
<221> NAME/KEY: SITE
<222> LOCATION: (1)..(5)
<223> OTHER INFORMATION: Description of Artificial Sequence: Caspase
      1,4,5 cleavage site
<220> FEATURE:
<221> NAME/KEY: VARIANT
<222> LOCATION: (1)
<223> OTHER INFORMATION: Xaa at position 1 can be W or L
<220> FEATURE:
<221> NAME/KEY: SITE
<222> LOCATION: (5)
<223> OTHER INFORMATION: Xaa at position 5 of the cleavage site can be
      any amino acid

<400> SEQUENCE: 19

Xaa Glu His Asp Xaa
 1               5

<210> SEQ ID NO 20
```

```
<211> LENGTH: 5
<212> TYPE: PRT
<213> ORGANISM: Artificial Sequence
<220> FEATURE:
<221> NAME/KEY: SITE
<222> LOCATION: (1)..(5)
<223> OTHER INFORMATION: Description of Artificial Sequence:Caspase
      2,3,7 cleavage site
<220> FEATURE:
<221> NAME/KEY: SITE
<222> LOCATION: (3)..(5)
<223> OTHER INFORMATION: Xaa at positions 3 and 5 in the cleavage site
      can be any amino acid

<400> SEQUENCE: 20

Asp Glu Xaa Asp Xaa
  1               5

<210> SEQ ID NO 21
<211> LENGTH: 5
<212> TYPE: PRT
<213> ORGANISM: Artificial Sequence
<220> FEATURE:
<221> NAME/KEY: SITE
<222> LOCATION: (1)..(5)
<223> OTHER INFORMATION: Description of Artificial Sequence:Caspase
      6,8,9 cleavage site
<220> FEATURE:
<221> NAME/KEY: VARIANT
<222> LOCATION: (1)
<223> OTHER INFORMATION: Xaa at position 1 can be L or V
<220> FEATURE:
<221> NAME/KEY: SITE
<222> LOCATION: (3)..(5)
<223> OTHER INFORMATION: Xaa at positions 3 and 5 of the cleavage site
      can be any amino acid

<400> SEQUENCE: 21

Xaa Glu Xaa Asp Xaa
  1               5

<210> SEQ ID NO 22
<211> LENGTH: 5
<212> TYPE: PRT
<213> ORGANISM: Artificial Sequence
<220> FEATURE:
<221> NAME/KEY: SITE
<222> LOCATION: (1)..(5)
<223> OTHER INFORMATION: Description of Artificial Sequence:Factor Xa
      cleavage site
<220> FEATURE:
<221> NAME/KEY: SITE
<222> LOCATION: (5)
<223> OTHER INFORMATION: Xaa at position 5 in the cleavage site can be
      any amino acid

<400> SEQUENCE: 22

Ile Glu Gly Arg Xaa
  1               5

<210> SEQ ID NO 23
<211> LENGTH: 7
<212> TYPE: PRT
<213> ORGANISM: Artificial Sequence
<220> FEATURE:
<221> NAME/KEY: SITE
<222> LOCATION: (1)..(7)
<223> OTHER INFORMATION: Description of Artificial Sequence:TEV protease
      cleavage site
<220> FEATURE:
<221> NAME/KEY: VARIANT
<222> LOCATION: (7)
<223> OTHER INFORMATION: Amino acid at position 7 can be S or G
```

```
<220> FEATURE:
<221> NAME/KEY: SITE
<222> LOCATION: (3)..(5)
<223> OTHER INFORMATION: Xaa at positions 3 and 5 of the cleavage site
      can be any amino acid

<400> SEQUENCE: 23

Glu Asn Xaa Tyr Xaa Gln Ser
 1               5

<210> SEQ ID NO 24
<211> LENGTH: 36
<212> TYPE: PRT
<213> ORGANISM: Saccharomyces cerevisiae

<400> SEQUENCE: 24

Arg Met Lys Gln Leu Glu Asp Lys Val Glu Glu Leu Leu Ser Lys Thr
 1               5                  10                  15

Tyr His Leu Glu Asn Glu Val Ala Cys Leu Lys Lys Leu Val Gly Glu
                20                  25                  30

Arg Ala Ala Lys
            35

<210> SEQ ID NO 25
<211> LENGTH: 25
<212> TYPE: PRT
<213> ORGANISM: Artificial Sequence
<220> FEATURE:
<223> OTHER INFORMATION: Description of Artificial Sequence:peptide for
      forming part of a heterodimeric coiled coil

<400> SEQUENCE: 25

Ile Ala Ala Leu Arg Glu Arg Ile Cys Tyr Leu Arg Glu Arg Asn Gln
 1               5                  10                  15

Gln Leu Arg Gln Arg Ile Gln Gln Leu
                20                  25

<210> SEQ ID NO 26
<211> LENGTH: 25
<212> TYPE: PRT
<213> ORGANISM: Artificial Sequence
<220> FEATURE:
<223> OTHER INFORMATION: Description of Artificial Sequence:peptide for
      forming coiled coil
<220> FEATURE:
<221> NAME/KEY: MOD_RES
<222> LOCATION: (1)
<223> OTHER INFORMATION: ACETYLATION
<220> FEATURE:
<221> NAME/KEY: MOD_RES
<222> LOCATION: (25)
<223> OTHER INFORMATION: AMIDATION

<400> SEQUENCE: 26

Ile Ala Ala Leu Arg Glu Arg Ile Cys Tyr Leu Arg Glu Arg Asn Gln
 1               5                  10                  15

Gln Leu Arg Gln Arg Ile Gln Gln Leu
                20                  25

<210> SEQ ID NO 27
<211> LENGTH: 33
<212> TYPE: PRT
<213> ORGANISM: Artificial Sequence
<220> FEATURE:
<223> OTHER INFORMATION: Description of Artificial Sequence:Peptide
      containing the TEV protease cleavage site.
```

<400> SEQUENCE: 27

Arg Met Lys Gln Leu Glu Asp Lys Val Glu Asn Leu Tyr Ser Gln Ser
 1               5                  10                  15

Tyr His Leu Glu Asn Glu Val Ala Cys Leu Lys Lys Leu Val Gly Glu
             20                  25                  30

Arg

<210> SEQ ID NO 28
<211> LENGTH: 34
<212> TYPE: PRT
<213> ORGANISM: Artificial Sequence
<220> FEATURE:
<223> OTHER INFORMATION: Description of Artificial Sequence:Coiled coil
      peptide derived from Saccharomyces cerevisiae GCN4
      that contains thrombin cleavage site.

<400> SEQUENCE: 28

Lys Met Lys Gln Leu Glu Asp Lys Val Arg Glu Leu Leu Ser Lys Asn
 1               5                  10                  15

Tyr His Leu Glu Asn Glu Val Ala Cys Leu Leu Lys Lys Leu Val Gly
             20                  25                  30

Glu Arg

<210> SEQ ID NO 29
<211> LENGTH: 33
<212> TYPE: PRT
<213> ORGANISM: Artificial Sequence
<220> FEATURE:
<223> OTHER INFORMATION: Description of Artificial Sequence: Coiled coil
      peptide adapted from Saccharomyces cerevisiae GCN4
      to contain a caspase cleavage site.

<400> SEQUENCE: 29

Arg Met Lys Gln Leu Glu Asp Lys Val Glu Glu Leu Leu Asp Glu Asn
 1               5                  10                  15

Asp His Leu Glu Asn Glu Val Ala Cys Leu Lys Lys Leu Val Gly Glu
             20                  25                  30

Arg

<210> SEQ ID NO 30
<211> LENGTH: 24
<212> TYPE: PRT
<213> ORGANISM: Artificial Sequence
<220> FEATURE:
<223> OTHER INFORMATION: Description of Artificial Sequence:Coiled coil
      peptide adapted from Saccharomyces cerevisiae GCN4
      to be substrate of geranylgeranyltransferase I.

<400> SEQUENCE: 30

Lys Val Glu Glu Leu Leu Ser Lys Asn Tyr His Leu Glu Asn Glu Val
 1               5                  10                  15

Ala Arg Leu Lys Cys Ala Leu Leu
             20

<210> SEQ ID NO 31
<211> LENGTH: 44
<212> TYPE: PRT
<213> ORGANISM: Artificial Sequence
<220> FEATURE:
<223> OTHER INFORMATION: Description of Artificial Sequence:Peptide
      construct for coiled coil derived from the folate
      receptor and the consensus for GPI anchor
      addition.

```
-continued

<400> SEQUENCE: 31

Trp Ile Gln Ala Leu Glu Gln Glu Ile Gln Ala Leu Glu Gln Glu Asn
 1               5                  10                  15

Ala Ala Leu Glu Lys Glu Ile Lys Lys Leu Glu Lys Glu Ile Ala Ala
            20                  25                  30

Leu Ala Ala Ile Ala Ala Leu Ala Ala Ala Ile
        35                  40

<210> SEQ ID NO 32
<211> LENGTH: 44
<212> TYPE: PRT
<213> ORGANISM: Artificial Sequence
<220> FEATURE:
<223> OTHER INFORMATION: Description of Artificial Sequence:Peptide
      construct for coiled coil derived from the folate
      receptor and the consensus for GPI anchor
      addition.

<400> SEQUENCE: 32

Lys Ile Gln Ala Leu Arg Gln Arg Ile Gln Ala Leu Arg Gln Arg Asn
 1               5                  10                  15

Gln Ala Leu Arg Gln Arg Ile Gln Ala Leu Arg Gln Arg Ile Gln Ala
            20                  25                  30

Leu Gln Gln Gln Ile Gln Ala Leu Gln Gln Gln Ile
        35                  40
```